(12) United States Patent
Tanabe et al.

(10) Patent No.: US 12,307,639 B2
(45) Date of Patent: May 20, 2025

(54) IMAGE PROCESSING METHOD, IMAGE PROCESSING DEVICE, AND PROGRAM

(71) Applicant: NIKON CORPORATION, Tokyo (JP)

(72) Inventors: Yasushi Tanabe, Fujisawa (JP); Daishi Tanaka, Konosu (JP); Mariko Hirokawa, Yokohama (JP); Makoto Ishida, Ageo (JP)

(73) Assignee: NIKON CORPORATION, Tokyo (JP)

( * ) Notice: Subject to any disclaimer, the term of this patent is extended or adjusted under 35 U.S.C. 154(b) by 413 days.

(21) Appl. No.: 17/638,539

(22) PCT Filed: Aug. 30, 2019

(86) PCT No.: PCT/JP2019/034192
§ 371 (c)(1),
(2) Date: Jul. 7, 2022

(87) PCT Pub. No.: WO2021/038847
PCT Pub. Date: Mar. 4, 2021

(65) Prior Publication Data
US 2022/0398701 A1 Dec. 15, 2022

(51) Int. Cl.
*G06T 5/94* (2024.01)
*A61B 3/12* (2006.01)
(Continued)

(52) U.S. Cl.
CPC ............... *G06T 5/94* (2024.01); *A61B 3/12* (2013.01); *G06T 5/20* (2013.01); *G06T 5/73* (2024.01);
(Continued)

(58) Field of Classification Search
CPC .... G06T 5/94; G06T 5/20; G06T 5/73; G06T 2207/10024; G06T 2207/30041;
(Continued)

(56) References Cited

U.S. PATENT DOCUMENTS

2014/0198298 A1 7/2014 Cheng et al.
2017/0084009 A1 3/2017 Higashi et al.
(Continued)

FOREIGN PATENT DOCUMENTS

JP 2003-299620 A 10/2003
JP 2008-229157 A 10/2008
(Continued)

OTHER PUBLICATIONS

Wahid et al., "An Efficient Preprocessing Step for Retinal Vessel Segmentation via Optic Nerve Head Exclusion," Advances in Computing and Data Sciences: Third International Conference, ICACDS 2019 on Apr. 12-13, 2019 in Ghaziabad, India, Jan. 1, 2019, vol. 1046, (pp. 228-239).
(Continued)

*Primary Examiner* — Tom Y Lu
*Assistant Examiner* — Pardis Sohraby
(74) *Attorney, Agent, or Firm* — Foley & Lardner LLP

(57) ABSTRACT

An image processing method, including: by a processor: acquiring a fundus image; performing a first enhancement processing on an image of at least a central region of the fundus image, and performing a second enhancement processing, which is different from the first enhancement processing, on an image of at least a peripheral region of the fundus image that is at a periphery of the central region; and generating an enhanced image of the fundus image on the basis of a first image obtained as a result of the first enhancement processing having been performed and a second image obtained as a result of the second enhancement processing having been performed.

14 Claims, 15 Drawing Sheets

(51) Int. Cl.
  *G06T 5/20* (2006.01)
  *G06T 5/73* (2024.01)
  *H04N 1/60* (2006.01)
  *H04N 1/64* (2006.01)

(52) U.S. Cl.
  CPC ............... *G06T 2207/10024* (2013.01); *G06T 2207/30041* (2013.01); *H04N 1/6008* (2013.01); *H04N 1/646* (2013.01)

(58) Field of Classification Search
  CPC ............ G06T 5/40; G06T 7/0012; G06T 2207/10101; G06T 2207/20021; G06T 2207/30101; H04N 1/6008; H04N 1/646; A61B 3/12
  USPC .......................................................... 382/274
  See application file for complete search history.

(56) References Cited

U.S. PATENT DOCUMENTS

| | | |
|---|---|---|
| 2017/0084042 A1 | 3/2017 | Nakamae |
| 2017/0091911 A1 | 3/2017 | Higashi et al. |
| 2017/0091912 A1 | 3/2017 | Nakamae et al. |
| 2017/0296049 A1* | 10/2017 | Uji ................ G06T 5/73 |
| 2017/0347881 A1 | 12/2017 | Noda |
| 2017/0347882 A1 | 12/2017 | Noda |
| 2020/0111240 A1* | 4/2020 | Gupta ............... G06T 11/00 |
| 2020/0250497 A1* | 8/2020 | Peng ............... G06V 10/764 |
| 2020/0359888 A1 | 11/2020 | Hirokawa et al. |
| 2021/0343006 A1* | 11/2021 | Yu ................ G06T 7/12 |
| 2022/0047159 A1* | 2/2022 | Xiong ............. A61B 3/0025 |
| 2022/0284577 A1* | 9/2022 | Saito ............... G06T 7/0012 |

FOREIGN PATENT DOCUMENTS

| | | |
|---|---|---|
| JP | 2017-189530 A | 10/2017 |
| JP | 6225255 B2 | 11/2017 |
| WO | WO-2016/103484 A1 | 6/2016 |
| WO | WO-2016/103489 A1 | 6/2016 |
| WO | WO-2019/130583 A1 | 7/2019 |

OTHER PUBLICATIONS

CN First Office Action issued in corresponding CN Application No. 201980101567.9 Dated Feb. 18, 2025 (21 pages).

* cited by examiner

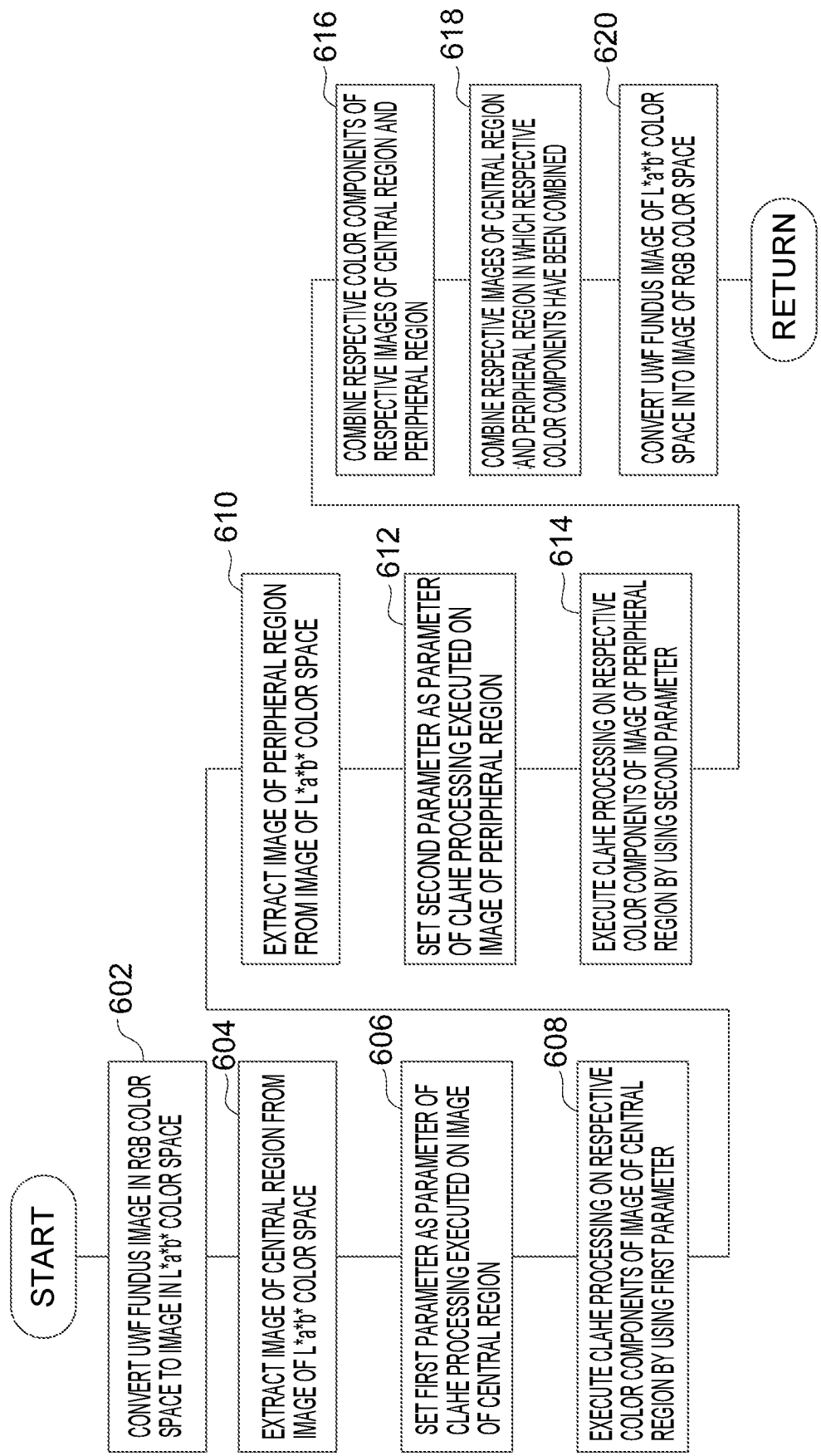

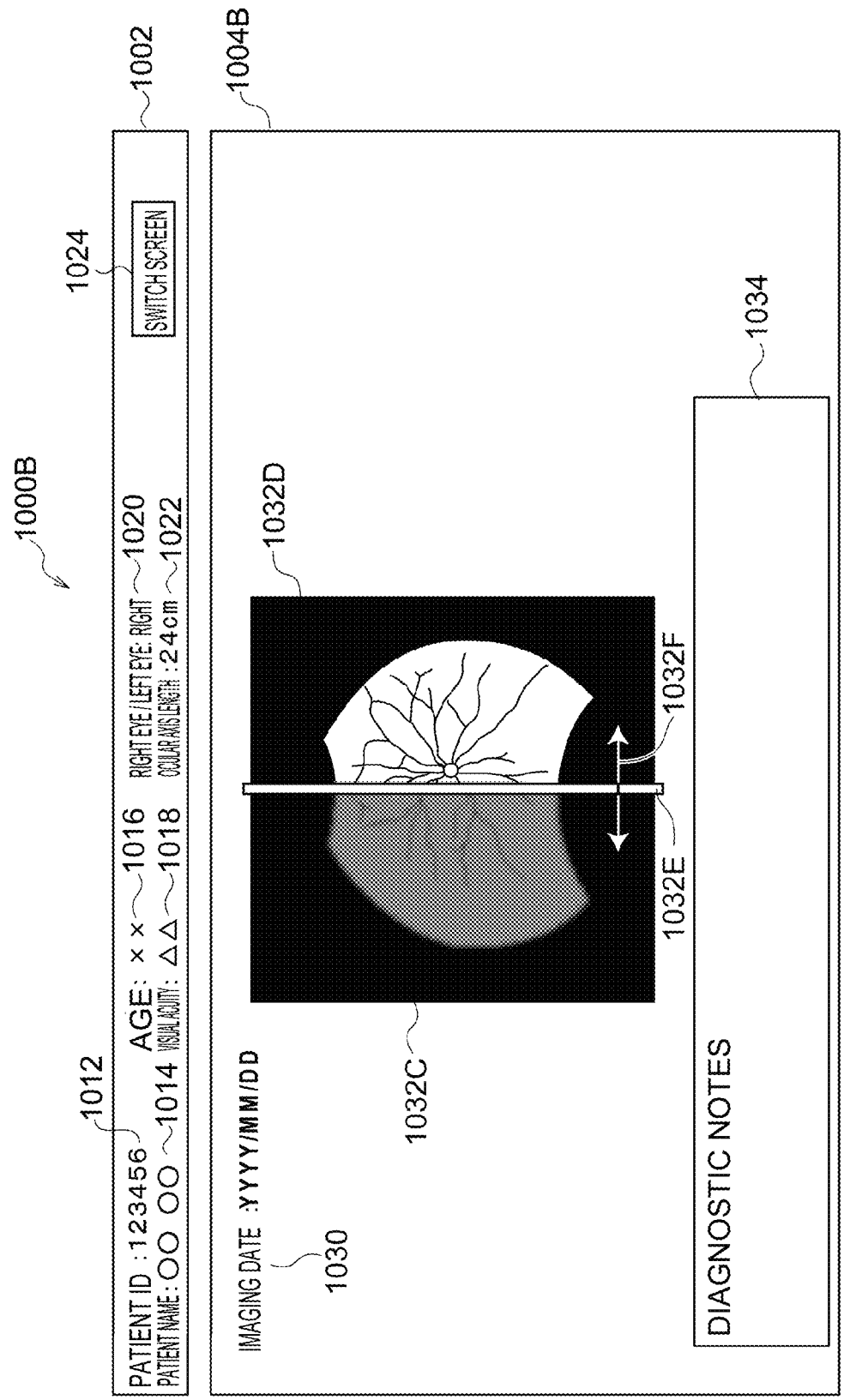

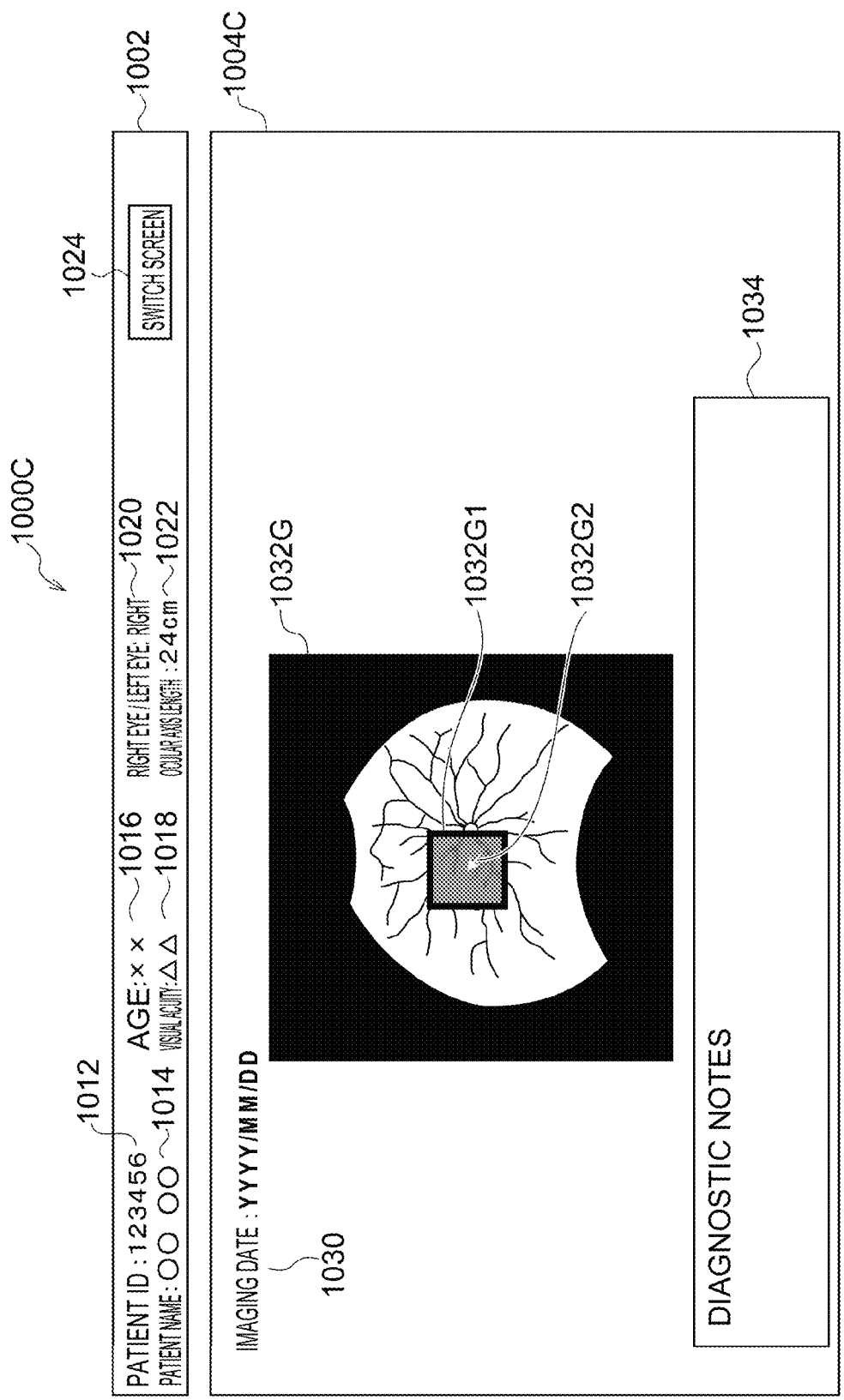

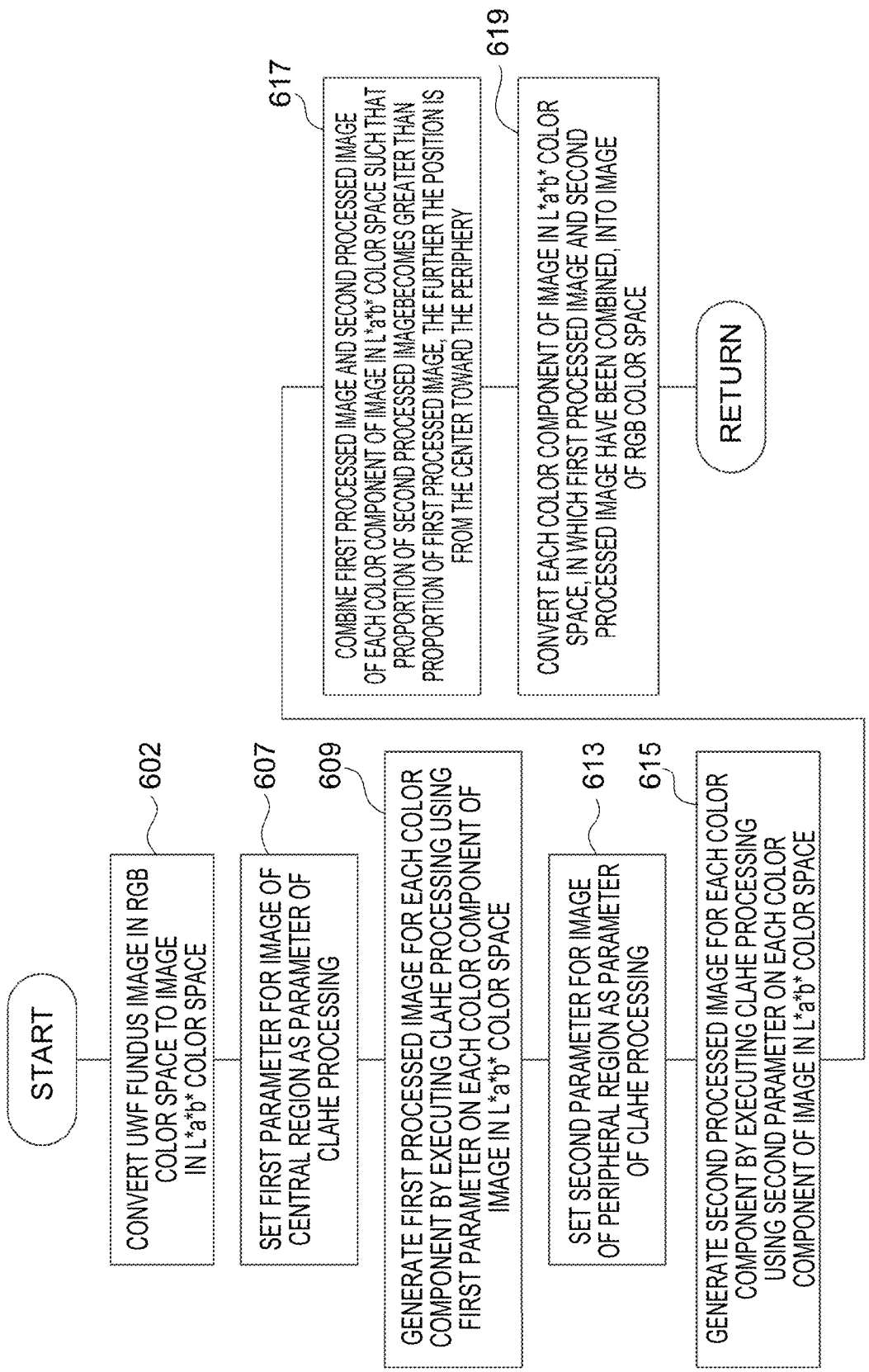

IMAGE PROCESSING METHOD, IMAGE PROCESSING DEVICE, AND PROGRAM

TECHNICAL FIELD

The present invention relates to an image processing method, an image processing device, and a program.

BACKGROUND ART

Japanese Patent Application Laid-Open (JP-A) No. 2008-229157 discloses an image processing technique that depicts blood vessel regions of a fundus image sharply. An image processing technique that sharpens fundus images is desired.

SUMMARY OF INVENTION

A first aspect of the technique of the present disclosure is an image processing method, including: by a processor: acquiring a fundus image; performing a first enhancement processing on an image of at least a central region of the fundus image, and performing a second enhancement processing, which is different from the first enhancement processing, on an image of at least a peripheral region of the fundus image that is at a periphery of the central region; and generating an enhanced image of the fundus image on the basis of a first image obtained as a result of the first enhancement processing having been performed and a second image obtained as a result of the second enhancement processing having been performed.

A second aspect of the technique of the present disclosure is an image processing method, including: by a processor: acquiring a fundus image; performing a first sharpening processing using a first parameter on the fundus image, and performing a second sharpening processing using a second parameter, which is different from the first parameter, on the fundus image; and generating a sharpened fundus image on the basis of an image obtained as a result of the first sharpening processing and the second sharpening processing having been performed.

An image processing device of a third aspect of the technique of the present disclosure includes a processor, and a memory coupled to the processor, the processor being configured to: acquire a fundus image; perform a first enhancement processing on an image of at least a central region of the fundus image, and perform a second enhancement processing, which is different from the first enhancement processing, on an image of at least a peripheral region of the fundus image that is at a periphery of the central region; and generate an enhanced image of the fundus image on the basis of a first image obtained as a result of the first enhancement processing having been executed and a second image obtained as a result of the second enhancement processing having been performed.

An image processing device of a fourth aspect of the technique of the present disclosure includes a processor, and a memory coupled to the processor, wherein the processor: acquires a fundus image; performs a first sharpening processing using a first parameter on the fundus image, and performs a second sharpening processing using a second parameter, which is different from the first parameter, on the fundus image; and generates a sharpened fundus image on the basis of an image obtained as a result of the first sharpening processing and the second sharpening processing having been performed.

A program of a fifth aspect of the technique of the present disclosure causes a computer to execute: acquiring a fundus image; performing a first enhancement processing on an image of at least a central region of the fundus image, and performing a second enhancement processing, which is different from the first enhancement processing, on an image of at least a peripheral region of the fundus image that is at a periphery of the central region; and generating an enhanced image of the fundus image on the basis of a first image obtained as a result of the first enhancement processing having been performed and a second image obtained as a result of the second enhancement processing having been performed.

A program of a sixth aspect of the technique of the present disclosure causes a computer to execute: acquiring a fundus image; performing a first sharpening processing using a first parameter on the fundus image, and performing a second sharpening processing using a second parameter, which is different from the first parameter, on the fundus image; and generating a sharpened fundus image on the basis of an image obtained as a result of the first sharpening processing and the second sharpening processing having been performed.

BRIEF DESCRIPTION OF DRAWINGS

FIG. 6A is a flowchart of the sharpening processing of step 504 of FIG. 5.

FIG. 13 is a drawing illustrating second fundus image display screen 1000B.

FIG. 14 is a drawing illustrating third fundus image display screen 1000C.

FIG. 15 is a flowchart of a modified example of the sharpening processing of step 504 of FIG. 5.

DESCRIPTION OF EMBODIMENTS

Embodiments of the present invention are described in detail hereinafter with reference to the drawings.

Figure 1:
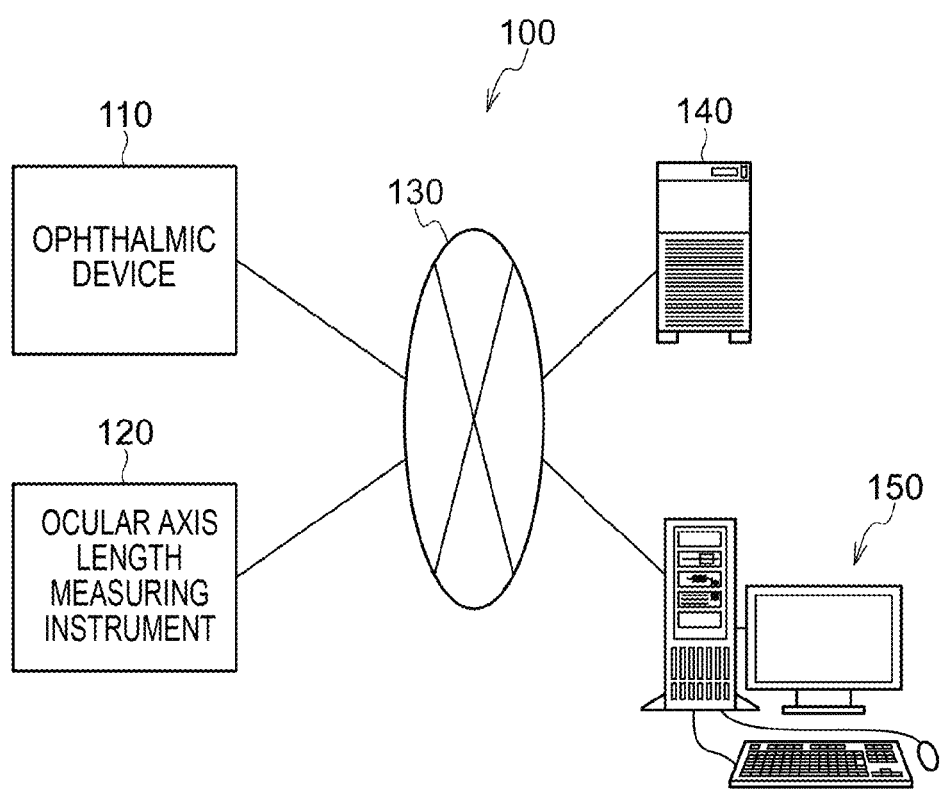
FIG. 1 a block drawing of an ophthalmic system 100.

The structure of an ophthalmic system 100 is described with reference to FIG. 1. As illustrated in FIG. 1, the ophthalmic system 100 has an ophthalmic device 110, an ocular axis length measuring instrument 120, a managing server device (hereinafter called "server") 140, and an image display device (hereinafter called "viewer") 150. The ophthalmic device 110 acquires a fundus image. The ocular axis length measuring instrument 120 measures the ocular axis length of a patient. The server 140 stores the fundus image, which is acquired by the fundus of the patient being imaged by the ophthalmic device 110, in correspondence with the ID of the patient. The viewer 150 displays medical information such as the fundus image acquired from the server 140, and the like.

The ophthalmic device 110, the ocular axis length measuring instrument 120, the server 140 and the viewer 150 are connected to one another via a network 130.

The structure of the ophthalmic device 110 is described next with reference to FIG. 2.

For convenience of explanation, a scanning laser ophthalmoscope is called "SLO". Further, optical coherence tomography is called "OCT".

Note that the horizontal direction, in a case in which the ophthalmic device 110 is set on a horizontal surface, is the "X direction", the direction orthogonal to the horizontal surface is the "Y direction", and the direction that connects the center of the pupil of the anterior eye portion of an subject eye 12 and the center of the eyeball is the "Z direction". Accordingly, the X direction, the Y direction and the Z direction are orthogonal to one another.

The ophthalmic device 110 includes an imaging device 14 and a control device 16. The imaging device 14 has a SLO unit 18, an OCT unit 20 and an imaging optical system 19, and acquires a fundus image of the fundus of the subject eye 12. Hereinafter, the two-dimensional fundus image that is acquired by the SLO unit 18 is called a SLO image. Further, the tomographic image or the directly frontal image (en-face image) or the like of the retina that is created on the basis of the OCT data acquired by the OCT unit 20 is called an OCT image.

The control device 16 has a computer having a CPU (Central Processing Unit) 16A, a RAM (Random Access Memory) 16B, a ROM (Read Only Memory) 16C, and an input/output port (I/O) 16D.

The control device 16 has an input/display device 16E that is connected to the CPU 16A via the I/O port 16D. The input/display device 16E has a graphic user interface that displays the image of the subject eye 12 and receives various instructions from the user. A touch panel display is an example of the graphic user interface.

Further, the control device 16 has an image processing device 16G that is connected to the I/O port 16D. The image processing device 16G generates an image of the subject eye 12 on the basis of data obtained by the imaging device 14. The control device 16 has a communication interface (I/F) 16F that is connected to the I/O port 16D. The ophthalmic device 110 is connected to the ocular axis length measuring instrument 120, the server 140 and the viewer 150 via the communication interface (I/F) 16F and the network 130.

As described above, in FIG. 2, the control device 16 of the ophthalmic device 110 has the input/display device 16E, but the technique of the present disclosure is not limited to this. For example, the control device 16 of the ophthalmic device 110 may not have the input/display device 16E, and may have a separate input/display device that is physically independent of the ophthalmic device 110. In this case, the display device has an image processing processor unit that operates under the control of the CPU 16A of the control device 16. The image processing processor unit may display the SLO image and the like on the basis of image signals that are outputted and instructed from the CPU 16A.

The imaging device 14 operates under the control of the CPU 16A of the control device 16. The imaging device 14 includes the SLO unit 18, the imaging optical system 19 and the OCT unit 20. The imaging optical system 19 includes a first optical scanner 22, a second optical scanner 24, and a wide angle optical system 30.

The first optical scanner 22 two-dimensionally scans, in the X direction and the Y direction, the light that exits from the SLO unit 18. The second optical scanner 24 two-dimensionally scans, in the X direction and the Y direction, the light that exits from the OCT unit 20. It suffices for the first optical scanner 22 and the second optical scanner 24 to be optical elements that can deflect light bundles, and, for example, polygon mirrors, galvano mirrors or the like can be used therefor. Further, the first optical scanner 22 and the second optical scanner 24 may be combinations of these.

The wide angle optical system 30 includes an objective optical system (not illustrated in FIG. 2) having a shared optical system 28, and a combining section 26 that combines the light from the SLO unit 18 and the light from the OCT unit 20.

Note that the objective optical system of the shared optical system 28 may be a reflective optical system that uses a concave mirror such as an elliptical mirror or the like, or a refractive optical system using a wide angle lens or the like, or a reflective/refractive optical system that combines a concave mirror and a lens. By using a wide angle optical system that uses an elliptical mirror or a wide angle lens or the like, not only the central portion of the fundus at which the optic papilla and the macula lutea exist, but also the retina of the fundus peripheral portion at which the equator of the eyeball and the vorticose veins exist, can be imaged.

Cases of using a system that includes an elliptical mirror may be structured so as to use the system using an elliptical mirror that is disclosed in International Publication WO 2016/103484 or International Publication WO 2016/103489. The respective disclosures of International Publication WO 2016/103484 and International Publication WO 2016/103489 are, in their entireties, incorporated by reference into the present specification.

Observation in a wide field of view (FOV) 12A at the fundus is realized by the wide angle optical system 30. The FOV 12A means the range in which imaging is possible by the imaging device 14. The FOV 12A can be expressed as the viewing angle. In the present embodiment, the viewing angle can be prescribed by the internal illumination angle and the external illumination angle. The external illumination angle is the illumination angle in which the illumination angle of the light bundle, which is illuminated from the ophthalmic device 110 toward the subject eye 12, is prescribed by using pupil 27 as the reference. Further, the internal illumination angle is the illumination angle in which the illumination angle of the light bundle, which is illuminated toward the fundus, is prescribed by using eyeball center O as the reference. The external illumination angle and the internal illumination angle have a corresponding relationship. For example, in a case in which the external illumination angle is 120°, the internal illumination angle corresponds to approximately 160°. In the present embodiment, the internal illumination angle is made to be 200°.

200° that is the internal illumination angle is an example of the "predetermined value" of the technique of the present disclosure.

Here the SLO fundus image that is obtained by carrying out imaging at an imaging field angle of 160° or more that is an internal illumination angle is called a UWF-SLO fundus image. Note that UWF is the abbreviation for ultra wide field.

Figure 2:
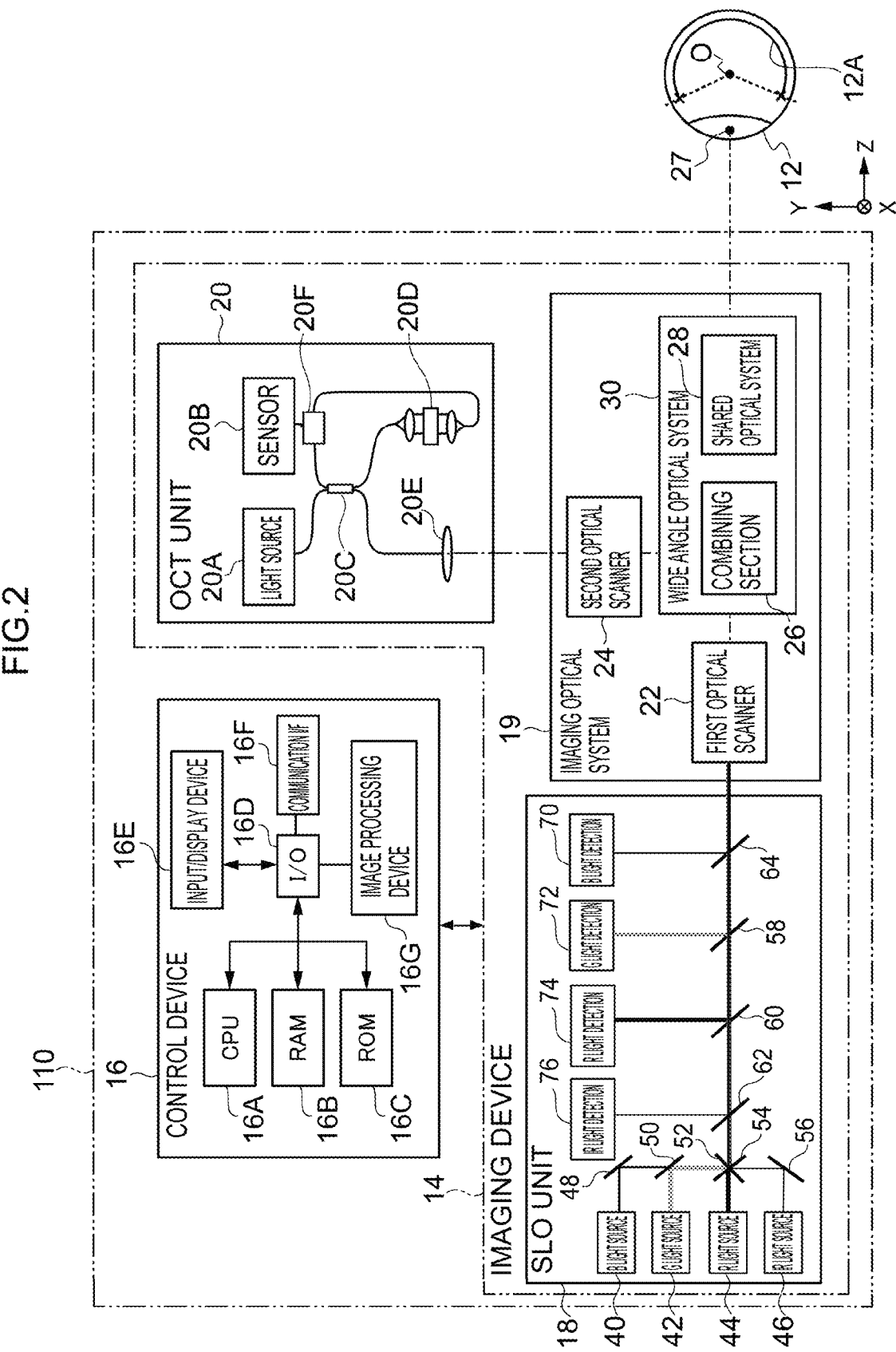
FIG. 2 is a schematic structural drawing illustrating the overall structure of an ophthalmic device 110.

A SLO system is realized by the control device 16, the SLO unit 18 and the imaging optical system 19 that are illustrated in FIG. 2. Because the SLO system has the wide angle optical system 30, the SLO system can capture images of the fundus in the wide FOV 12A.

The SLO unit 18 has plural light sources, e.g., a light source 40 of B light (blue color light), a light source 42 of G light (green color light), a light source 44 of R light (red color light), and a light source 46 of IR light (infrared light (e.g., near infrared light)), and has optical systems 48, 50, 52, 54, 56 that reflect or transmit the lights from the light sources 40, 42, 44, 46 and guide the lights to a single optical path. The optical systems 48, 50, 56 are mirrors, and the optical systems 52, 54 are beam splitters. The B light is reflected at the optical system 48, and transmitted through the optical system 50, and reflected at the optical system 54. The G light is reflected at the optical systems 50, 54. The R light is transmitted through the optical systems 52, 54. The IR light is reflected by the optical systems 56, 52. The respective lights are guided to a single optical path.

The SLO unit 18 is structured so as to be able to switch the combination of light sources that emit laser lights of different wavelengths or the light sources that are made to emit light such as a mode in which G light, R light and B light are emitted, a mode in which infrared light is emitted, and the like. In the example illustrated in FIG. 2, the four light sources that are the light source 40 of B light (blue color light), the light source 42 of G light, the light source 44 of R light, and the light source 46 of IR light are provided, but the technique of the present disclosure is not limited to this. For example, the SLO unit 18 may further have a light source of white light, and may emit light in various modes such as a mode in which only white light is emitted, or the like.

The light that is incident on the imaging optical system 19 from the SLO unit 18 is scanned in the X direction and the Y direction by the first optical scanner 22. The scanning light goes through the wide angle optical system 30 and the pupil 27, and is illuminated onto the posterior eye portion of the subject eye 12. The reflected light that is reflected by the fundus goes through the wide angle optical system 30 and the first optical scanner 22, and is made incident on the SLO unit 18.

The SLO unit 18 has a beam splitter 64 that, of the light from the posterior eye portion (e.g., the fundus) of the subject eye 12, reflects B light and transmits lights other than B light, and a beam splitter 58 that, of the light that is transmitted through the beam splitter 64, reflects G light and transmits lights other than G light. The SLO unit 18 has a beam splitter 60 that, of the light transmitted through the beam splitter 58, reflects R light and transmits light other than R light. The SLO unit 18 has a beam splitter 62 that, of the light transmitted through the beam splitter 60, reflects IR light.

The SLO unit 18 has plural light detecting elements in correspondence with the plural light sources. The SLO unit 18 has a B light detecting element 70 that detects the B light reflected by the beam splitter 64, and a G light detecting element 72 that detects the G light reflected by the beam splitter 58. The SLO unit 18 has an R light detecting element 74 that detects the R light reflected by the beam splitter 60, and an IR light detecting element 76 that detects the IR light reflected by the beam splitter 62.

In a case in which the light, which goes through the wide angle optical system 30 and the first optical scanner 22 and is made incident on the SLO unit 18 (the reflected light reflected by the fundus), is B light, the light is reflected at the beam splitter 64 and received by the B light detecting element 70. In the case of G light, the above-described incident light is transmitted through the beam splitter 64, reflected by the beam splitter 58, and received by the G light detecting element 72. In a case in which the above-described incident light is R light, the light is transmitted through the beam splitters 64, 58, is reflected by the beam splitter 60, and is received by the R light detecting element 74. In a case in which the above-described incident light is IR light, the light is transmitted through the beam splitters 64, 58, 60, is reflected by the beam splitter 62, and is received by the IR light detecting element 76. The image processing device 16G that operates under the control of the CPU 16A generates UWF-SLO images by using the signals detected at the B light detecting element 70, the G light detecting element 72, the R light detecting element 74 and the IR light detecting element 76.

The UWF-SLO images include a UWF-SLO image (G color fundus image) obtained by the fundus being imaged by G color, and a UWF-SLO image (R color fundus image) obtained by the fundus being imaged by R color. The UWF-SLO images include a UWF-SLO image (B color fundus image) obtained by the fundus being imaged by B color, and a UWF-SLO image (IR fundus image) obtained by the fundus being imaged by IR.

Further, the control device 16 controls the light sources 40, 42, 44 so as to emit light simultaneously. A G color fundus image, an R color fundus image and a B color fundus image whose respective positions correspond to one another are obtained due to the fundus of the subject eye 12 being imaged simultaneously by B light, G light and R light. An RGB color fundus image is obtained from the G color fundus image, the R color fundus image and the B color fundus image. Due to the control device 16 controlling the light sources 42, 44 so as to emit light simultaneously, and the fundus of the subject eye 12 being imaged simultaneously by G light and R light, a G color fundus image and an R color fundus image whose respective positions correspond to one another are obtained. An RG color fundus image is obtained from the G color fundus image and the R color fundus image.

In this way, specifically, there are a B color fundus image, a G color fundus image, an R color fundus image, an IR fundus image, an RGB color fundus image, and an RG color fundus image as the UWF-SLO images. The respective image data of the UWF-SLO images are, together with information of the patient that is inputted via the input/display device 16E, transmitted from the ophthalmic device 110 via the communication interface (I/F) 16F to the server 140. The respective image data of the UWF-SLO images and the information of the patient are stored in correspondence in a storage device 254. Note that examples of the information of the patient are the patient ID, name, age, visual acuity, designation of right eye/left eye and the like. An operator inputs the patient information via the input/display device 16E.

An OCT system is realized by the control device 16, the OCT unit 20 and the imaging optical system 19 that are illustrated in FIG. 2. Because the OCT system has the wide angle optical system 30, the OCT system can capture an image of the fundus in the wide FOV 12A, in the same way as the above-described capturing of a SLO fundus image. The OCT unit 20 includes a light source 20A, a sensor (detecting element) 20B, a first optical coupler 20C, a reference optical system 20D, a collimator lens 20E and a second optical coupler 20F.

The light that exits from the light source 20A is split at the first optical coupler 20C. One divisional light is made into parallel light at the collimator lens 20E as measurement light, and thereafter, is made incident on the imaging optical system 19. The measurement light is scanned in the X direction and the Y direction by the second optical scanner 24. The scanning light goes through the wide angle optical system 30 and the pupil 27, and is illuminated onto the fundus. The measurement light that is reflected by the fundus goes through the wide angle optical system 30 and the second optical scanner 24 and is made incident on the OCT unit 20, and, via the collimator lens 20E and the first optical coupler 20C, is incident on the second optical coupler 20F.

The other light, which exits from the light source 20A and is split-off at the first optical coupler 20C, is incident on the reference optical system 20D as reference light, and goes through the reference optical system 20D and is incident on the second optical coupler 20F.

These lights that are made incident on the second optical coupler 20F, i.e., the measurement light reflected at the fundus and the reference light, are made to interfere at the second optical coupler 20F, and interference light is generated. The interference light is received at the sensor 20B. On the basis of the OCT data detected at the sensor 20B, the image processing device 16G, which operates under the control of the CPU 16A, generates an OCT image that is a tomographic image or an en-face image or the like.

Here, the OCT fundus image, which is obtained by imaging at an imaging field angle of 160° or more that is an internal illumination angle, is called a UWF-OCT image.

The image data of the UWF-OCT image is, together with the information of the patient, transmitted from the ophthalmic device 110 via the communication interface (I/F) 16F to the server 140. The image data of the UWF-OCT image and the patient information are stored in the storage device 254 in correspondence with one another.

Note that, in the present embodiment, an example is given in which the light source 20A is SS-OCT (Swept-Source OCT), but the light source 20A may be any of various types of OCT systems such as SD-OCT (Spectral-Domain OCT), TD-OCT (Time-Domain OCT) or the like.

The ocular axis length measuring instrument 120 is described next. The ocular axis length measuring instrument 120 has two modes that are a first mode and a second mode that measure the ocular axis length that is the length of the subject eye 12 in the ocular axis direction. In the first mode, light from an unillustrated light source is guided to the subject eye 12, and thereafter, interference light of the reflected light from the fundus and the reflected light from the cornea is received, and the ocular axis length is measured on the basis of the interference signal that expresses the received interference light. The second mode is a mode in which the ocular axis length is measured by using unillustrated ultrasonic waves.

The ocular axis length measuring instrument 120 transmits the ocular axis length measured by the first mode or the second mode to the server 140. The ocular axis length may be measured by the first mode and the second mode, and, in this case, the average of the ocular axis lengths measured by the both modes is transmitted to the server 140 as the ocular axis length. The server 140 stores the ocular axis length of the patient in correspondence with the patient ID.

Figure 3:
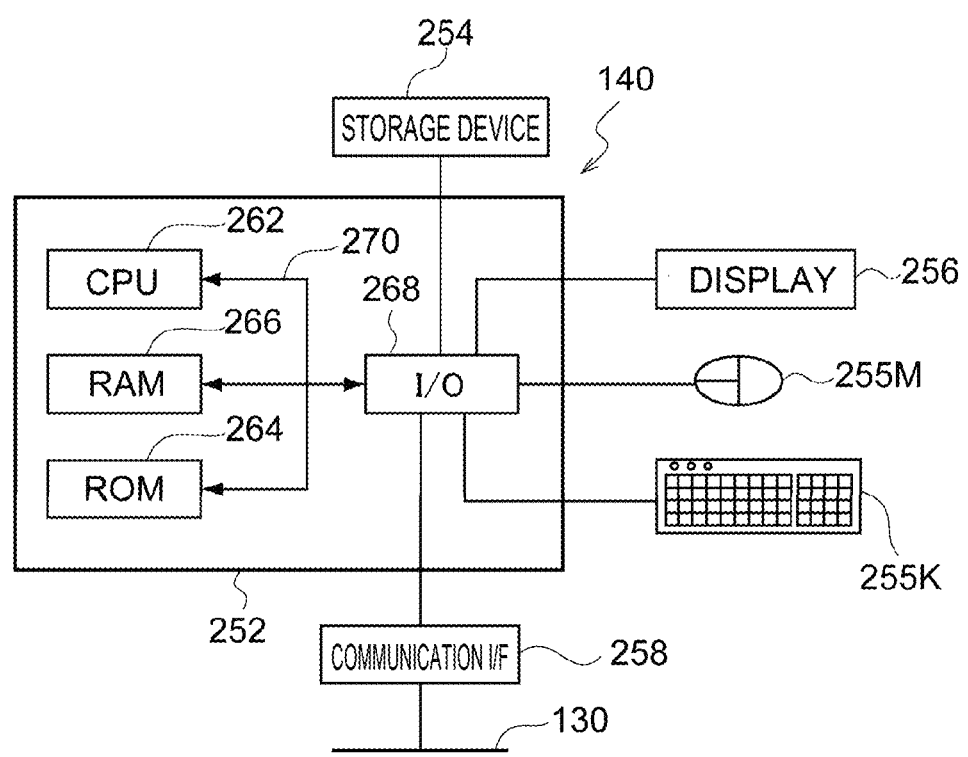
FIG. 3 is a block drawing of the structure of the electrical system of a server 140.

The structure of the electrical system of the server 140 is described next with reference to FIG. 3. As illustrated in FIG. 3, the server 140 has a computer main body 252. The computer main body 252 has a CPU 262, a RAM 266, a ROM 264 and an input/output (I/O) port 268 that are connected to one another by a bus 270. The storage device 254, a display 256, a mouse 255M, a keyboard 255K and a communication interface (I/F) 258 are connected to the input/output (I/O) port 268. The storage device 254 is structured by a non-volatile memory for example. The input/output (I/O) port 268 is connected to the network 130 via the communication interface (I/F) 258. Accordingly, the server 140 can communicate with the ophthalmic device 110 and the viewer 150. An image processing program that is described later is stored in the storage device 254. Note that the image processing program may be stored in the ROM 264.

The image processing program is an example of the "program" of the technique of the present disclosure. The storage device 254 and the ROM 264 are examples of the "memory" and the "computer-readable storage medium" of the technique of the present disclosure. The CPU 262 is an example of the "processor" of the present disclosure.

A processing section 208 (refer to FIG. 5 as well), which is described later, of the server 140 stores the respective data that are received from the ophthalmic device 110 in the storage device 254. Specifically, the processing section 208 stores the respective image data of the UWF-SLO images and the image data of the UWF-OCT image, and patient information (as described above, the patient ID and the like), in correspondence with one another in the storage device 254. Further, in a case in which there is a lesion at the subject eye of the patient, or in a case in which surgery has been carried out on a lesion portion, information relating to the lesion is inputted via the input/display device 16E of the ophthalmic device 110, and is transmitted to the server 140. The information of the lesion is stored in the storage device 254 in correspondence with the information of the patient. Information of the position of the lesion portion, the name of the lesion, the name of the surgery and the date and time of the surgery in a case in which the lesion portion has been operated on, and the like are information of the lesion.

The viewer 150 has a computer, which is equipped with a CPU, a RAM, a ROM and the like, and has a display. An image processing program is installed in the ROM. On the basis of instructions of the user, the computer controls the display such that medical information, such as the fundus image acquired from the server 140 and the like, are displayed on the display.

Figure 4:
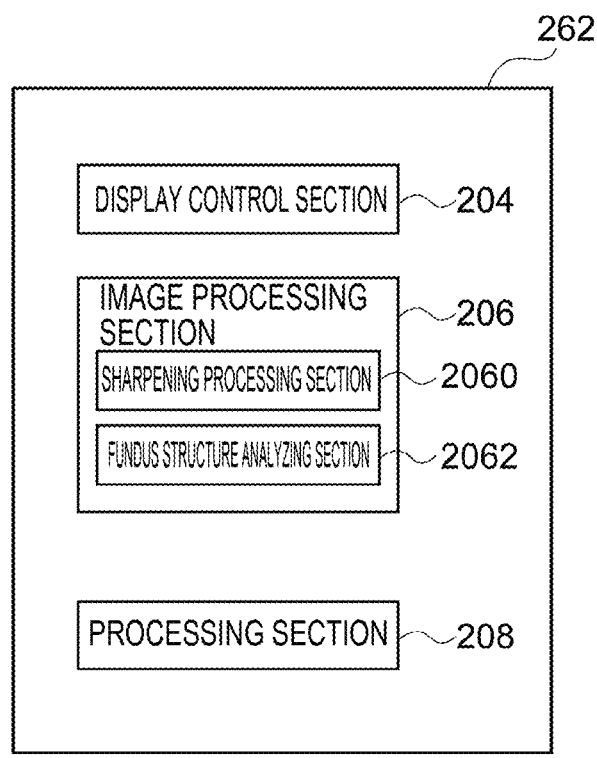
FIG. 4 is a block drawing of functions of a CPU 262 of the server 140.

Various functions, which are realized by the CPU 262 of the server 140 executing the image processing program, are described next with reference to FIG. 4. The image processing program has a display control function, image processing functions (a sharpening processing function, a fundus structure analyzing function), and a processing function. Due to the CPU 262 executing the image processing program that has these respective functions, as illustrated in FIG. 4, the CPU 262 functions as a display control section 204, an image processing section 206 (a sharpening processing section 2060, a fundus structure analyzing section 2062), and the processing section 208.

Figure 5:
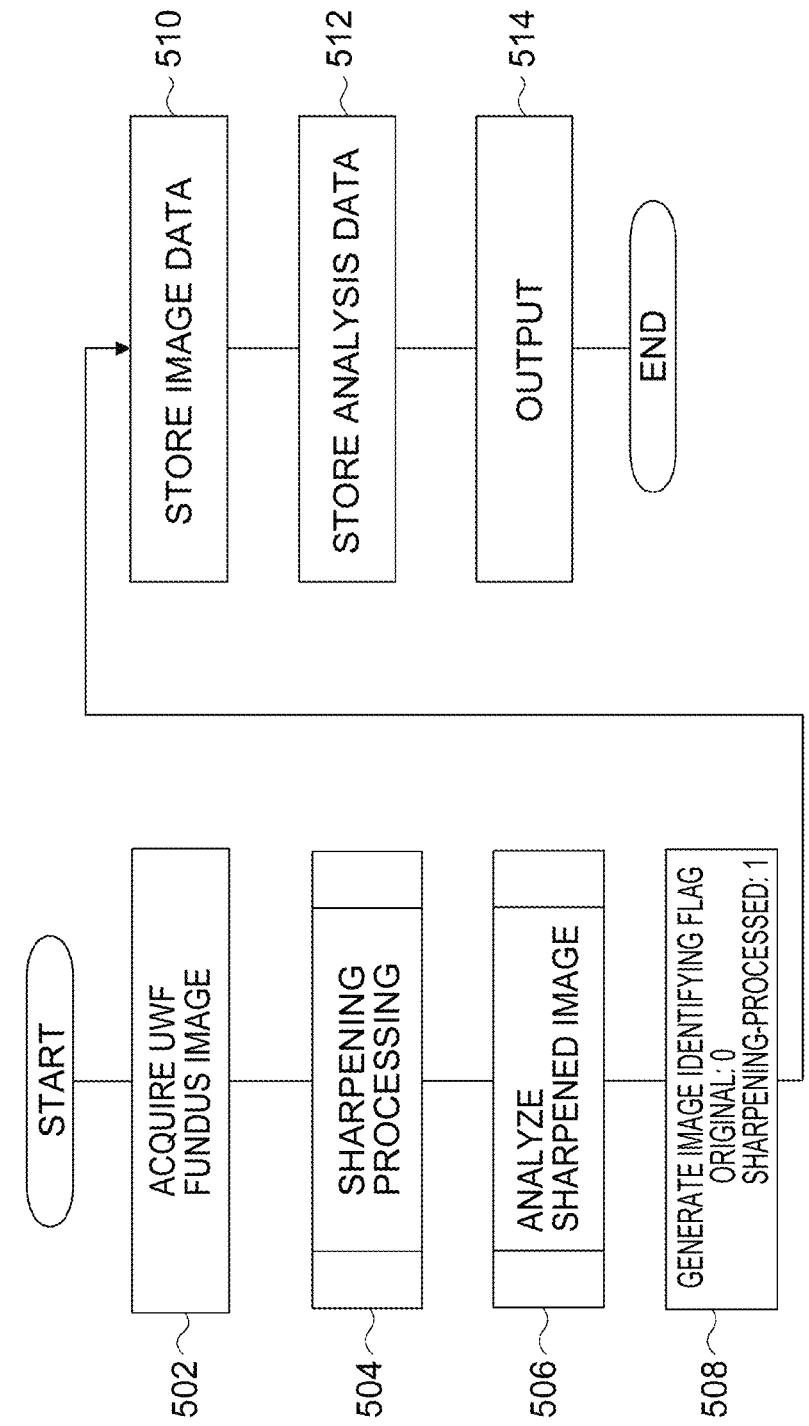
FIG. 5 is a flowchart of image processings by the server 140.

Next, the image processing by the server 140 is described in detail by using FIG. 5. Due to the CPU 262 of the server 140 executing the image processing program, the image processing illustrated in the flowchart of FIG. 5 is realized.

This image processing starts in a case in which a patient ID is inputted, and an unillustrated start button displayed on the display 256 is operated.

Figure 7:
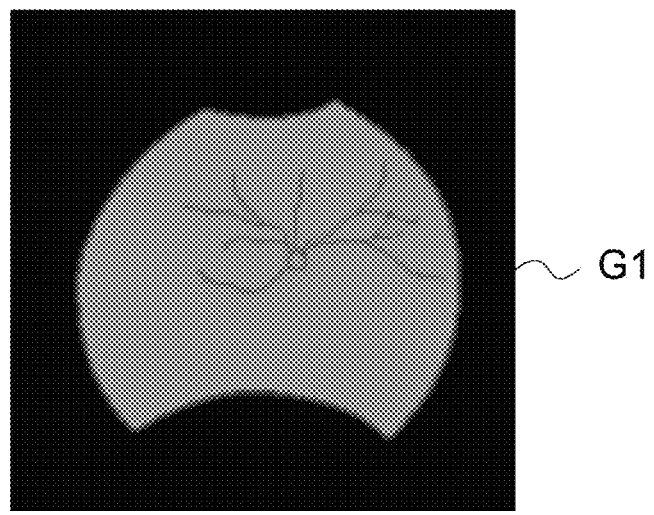
FIG. 7 is a drawing illustrating UWF fundus image G1 of the RGB color space.

In step 502, as illustrated in FIG. 7, the processing section 208 acquires UWF fundus image G1, which is stored in correspondence with the patient ID, from the storage device 254. The UWF fundus image G1 is the RGB color fundus image among the UWF-SLO images, and is a UWF fundus image in the RGB color space, and is the original UWF fundus image that has not been subjected to image processing.

In step 504, the sharpening processing section 2060 executes sharpening processing that is described in detail later. In step 506, the fundus structure analyzing section 2062 analyzes the sharpened image that is described in detail later.

In step 508, the processing section 208 generates image identifying flags, and sets image identifying flags for the original UWF fundus image (the UWF fundus image G1 (see FIG. 7)) and a post-sharpening-processing UWF fundus image. Specifically, the processing section 208 associates flag=0 with the original UWF fundus image. The processing section 208 associates flag=1 with the post-sharpening-processing UWF fundus image (the sharpened image).

In step 510, the processing section 208 stores the original UWF fundus image in correspondence with flag=0, and the sharpened image in correspondence with flag=1, in the storage device 254.

In step 512, the processing section 208 stores, in the storage device 254, data of the results of analysis that are obtained by the analysis executed by the fundus structure analyzing section 2062 on the post-sharpening-processing UWF fundus image.

In step 514, the processing section 208 outputs (transmits) the original UWF fundus image that is in a state of being associated with flag=0, and the post-sharpening-processing UWF fundus image that is in a state of being associated with flag=1, and analysis data to the viewer 150 via the communication interface 258.

Next, the sharpening processing of step 504 is executed with reference to FIG. 6A.

Figure 8A:
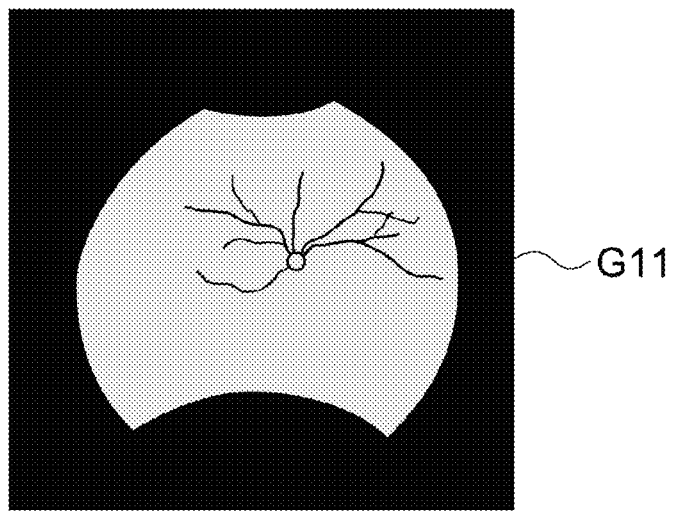
FIG. 8A is a drawing illustrating image G11 of the L* component of an image in the L*a*b* color space that is obtained by conversion of the UWF fundus image G1 of the RGB color space.

In step 602, the sharpening processing section 2060 converts the UWF fundus image G1 (see FIG. 7) of the RGB color space into images in the L*a*b* color space. Due thereto, an image G11 of the L* component (see FIG. 8A), an image of the a* component, and an image of the b* component are obtained.

The L*a*b* color space is an example of the "color space having three components that are a brightness component that expresses lightness, and a first color component and a second color component that are components of two different shades" of the technique of the present disclosure. The image G11 of the L* component (see FIG. 8A), the image of the a* component, and the image of the b* component respectively are fundus images, and therefore, a color space fundus image, which has three components that are brightness and two different shades, is acquired by the processing of step 602.

Namely, the RGB fundus image of the three primary color space (RGB) is converted into the Lab space fundus image of the complementary color space (L*a*b*), and the sharpening processing of step 504 is executed.
The complementary color space (L*a*b*) is also called the CIELAB color space or the "CIE 1976 L*a*b* color space".

Further, the RGB fundus image may be converted into the CIELUV color space (or the "CIE 1976 L*u*v* color space") that is another color space.

In order for the user to more effectively perceive the effects of the sharpening, it is better to carry out sharpening processing in the complementary color space (L*a*b*) in which perceived differences in color are converted into quantitative differences, and this is because the user (the observer (e.g., an ophthalmologist) who is viewing the image) can more effectively perceive the effects of sharpening. Namely, it is better to separate the image into a brightness component and color components that are perceptually independent in the complementary color space (L*a*b*), and to carry out sharpening processing independently on the respective components, than to carry out processing on the respective R, G, B color components in the RGB color space. Accordingly, an image in which the perceived differences can be experienced effectively can be generated by sharpening processing in the complementary color space (L*a*b*). Accordingly, it is preferable that the sharpening processing of the technique of the present disclosure be carried out with the image having been converted into the complementary color space (L*a*b*).

Figure 8B:
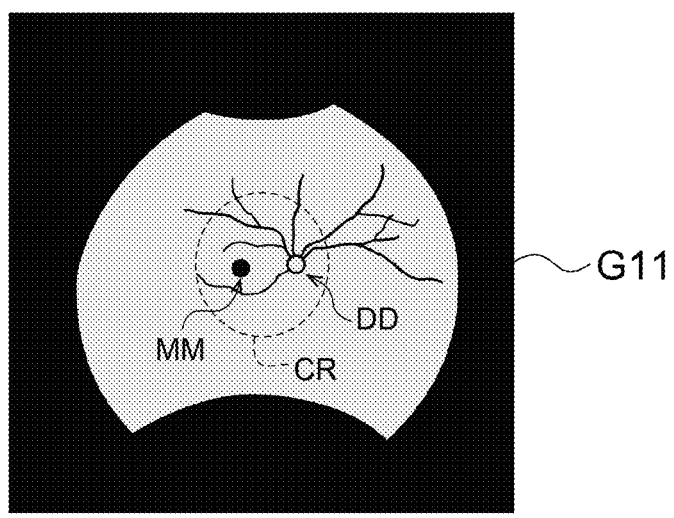
FIG. 8B is a drawing illustrating a central region and a peripheral region of the fundus image.

In step 604, the sharpening processing section 2060 extracts an image of a circular region of a predetermined radius whose center is the center of the image in the L*a*b* color space, from each image in the L*a*b* color space, as an image of the central region. Here, the central region is the region that includes the optic disc and the macula in the fundus image, and is the posterior pole portion of the fundus. The peripheral region is the region at the outer side of the central region, and is the equator and the peripheral portion of the fundus. Specifically, as illustrated in FIG. 8B, the region, which is surrounded by the dotted-line circle and includes optic disc DD and macula MINI, is central region CR, and the outer side of this dotted-line circle is the peripheral region.

Note that the central position of an image in the L*a*b* color space is the position at which the fundus of the subject eye 12 and the optical axis intersect.

In step 606, the sharpening processing section 2060 sets a first parameter as the parameter for CLAHE processing that is executed on the image of the central region.

Here, CLAHE (Contrast Limited Adaptive Histogram Equalization) processing is processing in which an image is divided into plural regions, and histogram equalization is carried out locally per divisional region, and, at the borders of the respective regions, interpolation processing such as bilinear interpolation or the like is carried out, thereby adjusting the contrast of the image.

Tile size is a parameter in CLAHE Processing. CLAHE processing is executed locally on an image (an image in the L*a*b* color space). Specifically, the image is divided into plural, quadrangular regions, and CLAHE processing is executed on each of the divisional regions. Each of these regions is called a tile, and the size of the tile is called the tile size.

Figure 9:
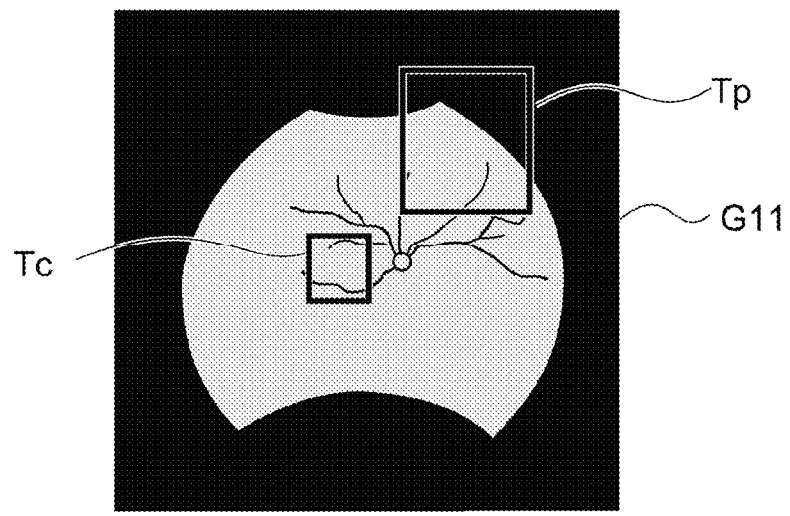
FIG. 9 is a drawing illustrating first tile size Tc for CLAHE processing on an image of the central region of the image G11 of the L* component, and second tile size Tp for CLAHE processing on an image of the peripheral region.

In the present embodiment, in step 606, the sharpening processing section 2060 sets first tile size Tc as the tile size as illustrated in FIG. 9. Although described in detail later, the sharpening processing section 2060 sets a second tile size Tp for the image of the peripheral region that is at the periphery of the central region. For the second tile size Tp that is used in CLAHE processing of the peripheral region, it is good for the length of one side of the tile (assuming that the tile is square) to be 1.4 times, and, in terms of surface area, to be 2 times the first tile size Tc that is used in CLAHE processing of the central region. Namely, the size of the first tile size Tc is smaller than the second tile size Tp. This is because, in order to capture an image of the fundus that is spherical, the peripheral region has distortion with respect to the central region.

In the original UWF fundus image G1 (FIG. 7) that is obtained by imaging in an imaging field angle of 160° or more that is an internal illumination angle as described above, distortion of the image is greater at the peripheral region than at the central region. In other words, the surface area of the actual fundus, which corresponds to a portion of the same predetermined surface area in the original UWF fundus image G1, is greater at the peripheral region than at the central region.

Thus, in the present embodiment, the second tile size Tp is made to be a size that is greater than the first tile size Tc.

Specifically, $Tp=n^2Tc$, given that the surface area of the actual fundus that corresponds to a portion of the central region in the original UWF fundus image G1 is Sc, and that the surface area of the actual fundus that corresponds to a portion of the peripheral region in the original UWF fundus image G1 is Sp, and that $Sp=n^2Sc$.

Accordingly, the degree of enhancement by CLAHE processing with respect to the respective L*a*b* components of the image of the peripheral region, is made to be greater than the degree of enhancement by CLAHE processing with respect to the respective L*a*b* components of the image of the central region.

In step 608, the sharpening processing section 2060 executes CLAHE processing by using the first parameter, on the respective L*a*b* components of the image of the central region.

In step 610, the sharpening processing section 2060 extracts the image of the region other than the central region, from the images of the L*a*b* color space, as the image of the peripheral region.

In step 612, the sharpening processing section 2060 sets a second parameter as the parameter of the CLAHE processing that is to be executed on the image of the peripheral region. In the present embodiment, the sharpening processing section 2060 sets the second tile size Tp, whose size is greater than the first tile size Tc, as the tile size.

In step 614, the sharpening processing section 2060 executes CLAHE processing by using the second parameter, on the images of the peripheral regions of the respective L*a*b* components of the image of the peripheral region.

In step 616, the sharpening processing section 2060 combines the respective components of the respective images of the central region and the peripheral region. In step 618, the sharpening processing section 2060 combines the respective images of the central region and the peripheral region whose respective components have been combined. Due thereto, a sharpened UWF fundus image of the L*a*b* color space is obtained.

Figure 10:
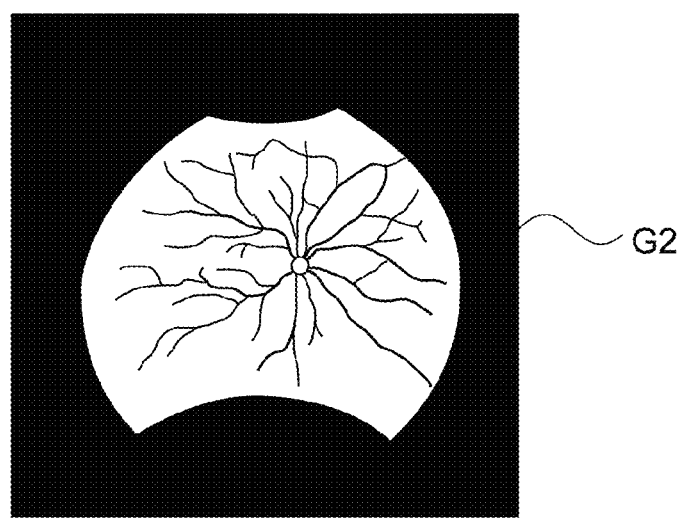
FIG. 10 is a drawing illustrating UWF fundus image G2 of the RGB color space after sharpening processing.

In step 620, the sharpening processing section 2060 converts the sharpened UWF fundus image of the L*a*b* color space into image G2 of the RGB color space, as illustrated in FIG. 10.

In the image G2 of the RGB color space (FIG. 10), the blood vessels are sharper than in the original UWF fundus image G1 (FIG. 7), and the blood vessels, which were difficult to see in the original UWF fundus image G1, can be seen. Further, lesion portions, such as hemorrhages, white spots, retinal detachment, and the like also are sharp.

Figure 6B:
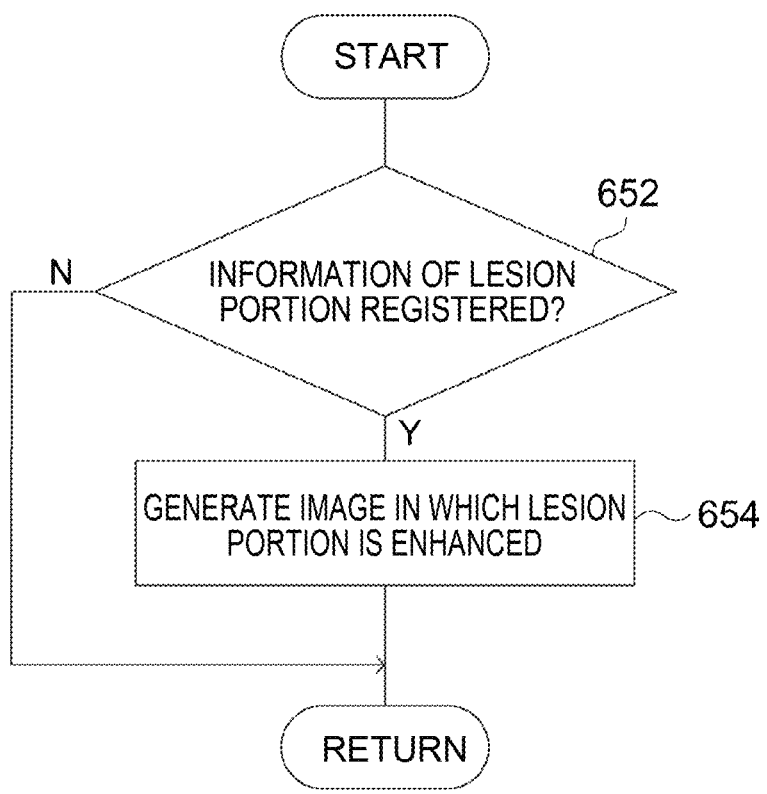
FIG. 6B is a flowchart of the analyzing processing of a sharpened image of step 506 of FIG. 5.

Next, the analyzing processing of the sharpened image of step 506 is described with reference to FIG. 6B.

In step 652, the fundus structure analyzing section 2062 judges whether or not information of a lesion has been registered in correspondence with the ID of the patient who is the current subject.

In a case in which information of a lesion has not been registered in correspondence with the ID of the patient who is the current subject, the analyzing processing ends.

In a case in which information of a lesion has been registered in correspondence with the ID of the patient who is the current subject, the fundus structure analyzing section 2062 generates an enhanced image in which the lesion region is enhanced, and stores the enhanced image in the storage device 254 as analysis data.

Figure 11:
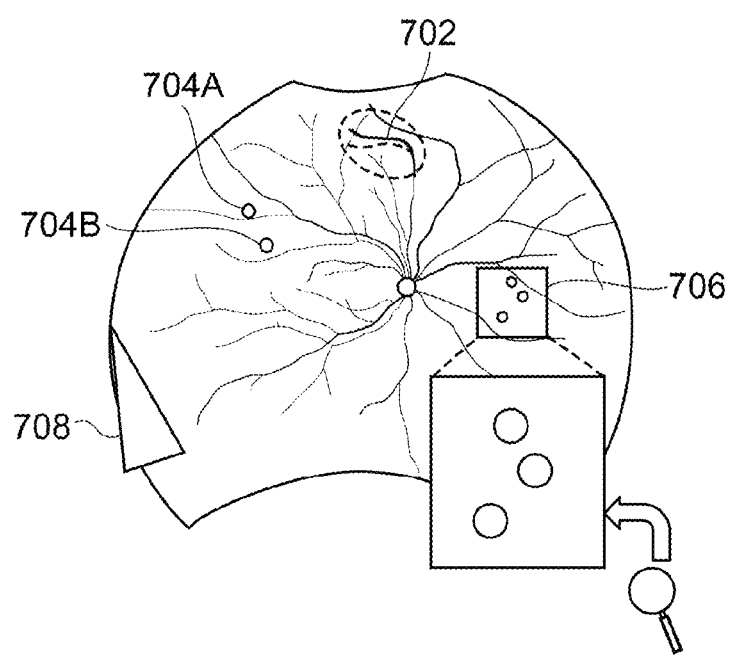
FIG. 11 is a drawing illustrating an enhanced image in which lesion portions have been enhanced.

As described above, in step 508 of FIG. 5, analysis data also is outputted (transmitted) to the viewer 150. Therefore, the image, which is illustrated in FIG. 11 and in which lesion portions are enhanced, is displayed at the viewer 150. Due thereto, the lesion portions are made visible.

For example, first, in a case in which there is a lesion portion at the vitreous body, and that lesion portion is being operated on, as illustrated in FIG. 11, the fundus structure analyzing section 2062 generates an enhanced image in which the color of the retina blood vessels of surgical site 702 is changed or the retina blood vessels before the surgery are superposed.

The viewer 150 displays the enhanced image in accordance with the instructions of the ophthalmologist at the time of examining the subject eye. The viewer 150 displays the retina blood vessels of the surgical site 702 while changing the color thereof, or while superposing the retina blood vessels of the surgical site 702 and the retina blood vessels before surgery. Due thereto, the positional offset between the retina blood vessels of the surgical site 702 and the retina blood vessels before surgery can be confirmed. The viewer 150 may display only the retina blood vessels after surgery the surgical site 702, or may display only the retina blood vessels before surgery of the surgical site 702, or may display these alternately.

Second, in a case in which there is a retinal detachment lesion, the fundus structure analyzing section 2062 creates an enhanced image in which a red frame is superposed on place 708 of the retinal detachment.

The viewer 150 displays the enhanced image in accordance with the instructions of the ophthalmologist at the time of examining the subject eye. In this case, the viewer 150 may display the place 708 of the retinal detachment so as to flash, or may display the place 708 so as to flash inversely, or may display the position and the size thereof.

Third, in a case in which there is the lesion of dot hemorrhages, the fundus structure analyzing section 2062 creates an enhanced image in which the color of place 706 of the dot hemorrhages is changed or in which, instead of or together with changing the color, the number of places of dot hemorrhages is superposed.

The viewer 150 displays the enhanced image in accordance with the instructions of the ophthalmologist at the time of examining the subject eye. In this case, the viewer 150 may display the place 706 of the dot hemorrhages so as to flash, or may display the place 706 so as to flash inversely, or may display the counted value of the number thereof. In a case in which the vicinity of the place 706 of the dot hemorrhages is clicked-on, the viewer 150 may display a magnifying glass button M, and, when the magnifying glass button is pushed, the viewer 150 may display the place 706 of the dot hemorrhages in an enlarged manner.

Fourth, in a case in which there are white spot lesions, the fundus structure analyzing section 2062 creates an enhanced image in which the color of places 704A, 704B of the white spots is changed or in which, instead of or together with changing the color, the number of white spots is superposed.

The viewer 150 displays the enhanced image in accordance with the instructions of the ophthalmologist at the time of examining the subject eye. In this case, the viewer 150 may display the places 704A, 704B of the white spots so as to flash, or may display the places 704A, 704B so as to flash inversely.

At the time of examining the subject eye of the patient, the ophthalmologist inputs the patient ID to the viewer 150. The viewer 150 instructs the server 140 to transmits image data and the like of the subject eye corresponding to the patient ID. The server 140 transmits the patient name, the age of the patient, the visual acuity of the patient, information as to whether the eye is the left eye or the right eye, the ocular axis length, the date of imaging, and the image data, which correspond to the patient ID, to the viewer 150 together with the patient ID.

Figure 12:
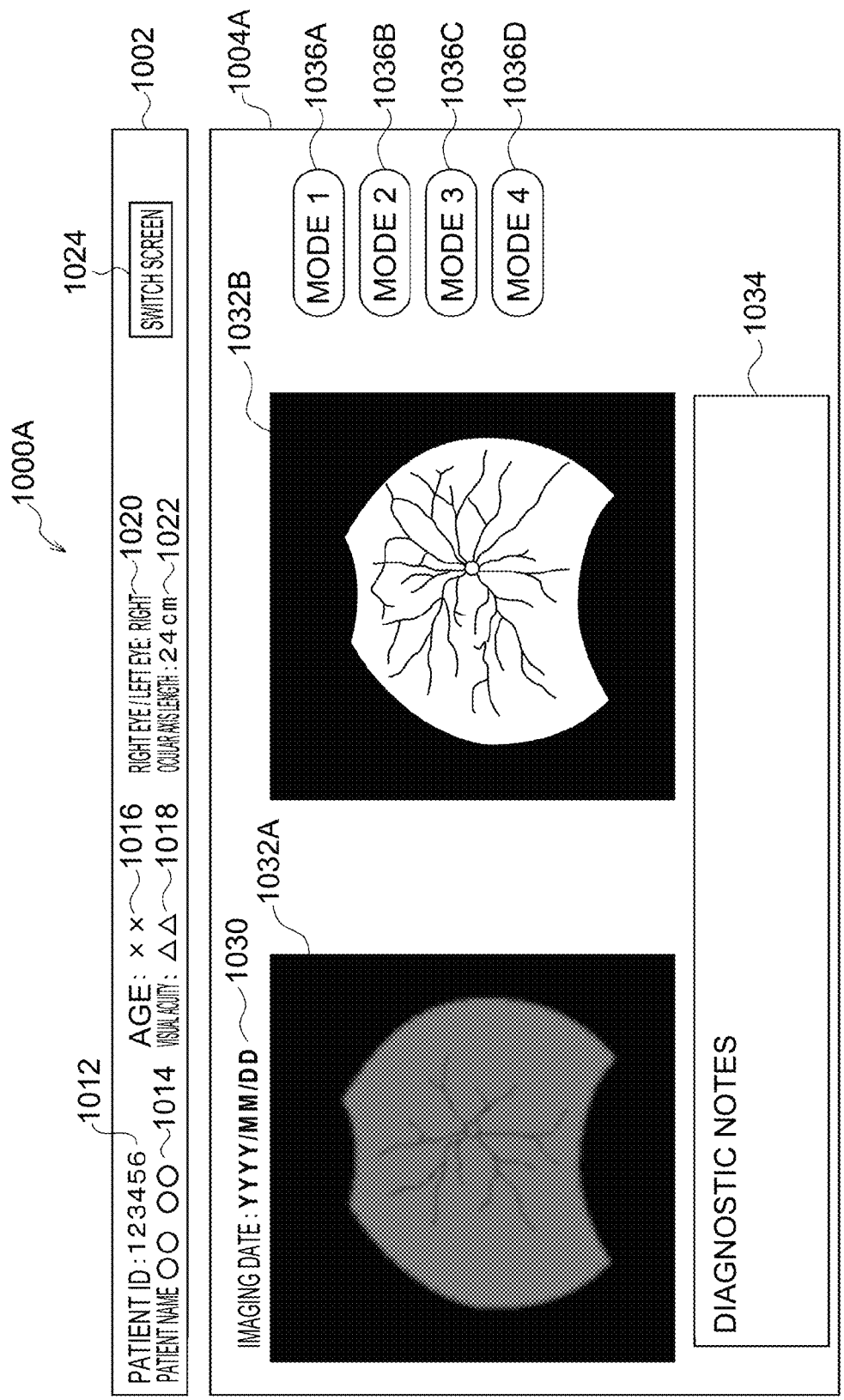
FIG. 12 is a drawing illustrating first fundus image display screen 1000A.

The viewer 150, which receives the patient ID, the patient name, the age of the patient, the visual acuity of the patient, information as to whether the eye is the left eye or the right eye, the ocular axis length, the date of imaging and the image data, displays a first fundus image display screen 1000A that is illustrated in FIG. 12 on the display.

As illustrated in FIG. 12, the first fundus image display screen 1000A has a patient information display box 1002 and a first fundus image information display box 1004A.

The patient information display box 1002 has respective display fields 1012 through 1022 for displaying the patient ID, the patient name, the age of the patient, the visual acuity of the patient, information as to whether the eye is the left eye or the right eye, and the ocular axis length, and a screen switching button 1024. The received patient ID, patient name, age of the patient, visual acuity of the patient, information as to whether the eye is the left eye or the right eye, and ocular axis length are displayed in the display fields 1012 through 1022.

The first fundus image information display box 1004A has an imaging date display box 1030, an original UWF fundus image display box 1032A, a post-sharpening-processing UWF fundus image display box 1032B, an information display box 1034, and select buttons 1036A through 1036D.

The imaging date (YYY/MM/DD) is displayed in the imaging date display box 1030. Comments and memos at the time of examination by the user (the ophthalmologist) are displayed as text in the information display box 1034.

The original UWF fundus image G1 (FIG. 7) is displayed in the original UWF fundus image display box 1032A. The post-sharpening-processing UWF fundus image G2 (FIG. 10) is displayed in the post-sharpening-processing UWF fundus image display box 1032B.

Mode 1, which is selected by the select button 1036A, is a mode for camera-like correction of fundus image shades. The mode for camera-like correction of fundus image shades is a mode that changes the shades of the post-sharpening-processing UWF fundus image G2, which is displayed in the post-sharpening-processing UWF fundus image display box 1032B, to the shades of an image that is obtained by imaging by the fundus camera.

Mode 2 that is selected by the select button 1036B is a haze removal processing mode. The haze removal processing mode is a mode of processing (haze removal processing) that removes haze (e.g., fogging or the like) from the post-sharpening-processing UWF fundus image G2. Haze removal processing is disclosed in the following thesis and patent document and the like.

(Thesis)
He, Kaiming. "Single Image Haze Removal Using Dark Channel Prior." Thesis, The Chinese University of Hong Kong, 2011.
(Patent Document)
Japanese Patent No. 6225255

Mode 3 that is selected by the select button 1036C is a pachychoroid (choroidal thickening) confirming mode. The pachychoroid confirming mode is a mode in which, in the post-sharpening-processing UWF fundus image G2 that is displayed in the post-sharpening-processing UWF fundus image display box 1032B, the proportion of the red component is enhanced more than the proportions of the other color (green, blue) components. For example, if the select button 1036C of mode 3 is operated in a case in which the red, green, blue components are equal in the post-sharpening-processing UWF fundus image G2, the proportion of the red component is made to be 80%, and the respective proportions of the other color (green, blue) components are made to be 10%, or the like. When the proportion of the red component is enhanced more than the proportions of the other color (green, blue) components in the post-sharpening-processing UWF fundus image G2, the red color light passes through the retina and reaches the choroid, and therefore, the blood vessel portions of the choroid are enhanced more than the blood vessels of the retina. Due thereto, the state of pachychoroid (choroidal thickening) can be confirmed.

The object of the image processing that is carried out in order to confirm the state of pachychoroid (choroidal thickening) in this way may be, instead of the post-sharpening-processing UWF fundus image G2, the UWF fundus image G1 in the RGB color space (see FIG. 7) as follows. Specifically, first, information of the red (R) component of the UWF fundus image G1, which is based on the R light that passes through the retina and reaches the choroid, includes information of the blood vessels of the retina and the choroid respectively. Information of the green (G) component of the UWF fundus image G1, which is based on the G light that only reaches as far as the retina, does not include information of the blood vessels of the choroid, and includes information of the blood vessels of the retina. The blood vessels of the choroid are extracted from the above-described information of the red (R) component and the above-described information of the green (G) component. Then, separately from the image processing of FIG. 5, the processing section 208 of the server 140 extracts the blood vessels of the choroid from the UWF fundus image G1 of the RGB color space (see FIG. 7), and stores them in the storage device 254. In a case in which the select button 1036C for mode 3 is operated, the viewer 150 receives information of the choroid blood vessels from the server 140, and superposes them on the post-sharpening-processing UWF fundus image G2 that is displayed in the post-sharpening-processing UWF fundus image display box 1032B.

Mode 4 that is selected by the select button 1036D is a vitreous body surgical results confirming mode. The vitreous body surgical results confirming mode is a mode that enhances the proportion of the green component more than the proportions of the components of the other color (red, blue) components in the post-sharpening-processing UWF fundus image G2 that is displayed in the post-sharpening-processing UWF fundus image display box 1032B. For example, if the select button 1036D of mode 4 is operated in a case in which the red, green, blue components are equal in the post-sharpening-processing UWF fundus image G2, the proportion of the green component is made to be 80%, and the respective proportions of the other color (red, blue)

components are made to be 10%, or the like. When the proportion of the green color component is enhanced more than the proportions of the other color (red, blue) components in the post-sharpening-processing UWF fundus image G2, because the green color light does not pass through the retina and does not reach the choroid, only the blood vessels of the retina are enhanced. Due thereto, the post-surgical state of blood vessels of the retina, which is the object of vitreous body surgery, can be confirmed.

In a case in which the select button 1036A through 1036D is operated, the viewer 150 executes the above-described processing that corresponds to the mode, on the post-sharpening-processing UWF fundus image G2 that is displayed in the post-sharpening-processing UWF fundus image display box 1032B. The viewer 150 displays, in the UWF fundus image display box 1032B, the post-sharpening-processing UWF fundus image that has been subjected to the above-described processing corresponding to the mode.

The technique of the present disclosure is not limited to the above-described processings, which correspond to the modes, being executed by the viewer 150 in this way. For example, first, the viewer 150 may instruct the server 140 to carry out processing corresponding to the mode, and the server 140 may execute that processing. The server 140 transmits the post-sharpening-processing UWF fundus image that has been subjected to that processing to the viewer 150, and the viewer 150 displays the post-sharpening-processing UWF fundus image that has been subjected to that processing in the UWF fundus image display box 1032B.

Moreover, other than the viewer 150 and the server 140, a separate imaging processing device that is further connected to the network 130 may execute the processings corresponding to the modes.

Note that the post-sharpening-processing UWF fundus image, which has been subjected to the above-described processing corresponding to the mode, may be displayed together with the post-sharpening-processing UWF fundus image G2.

In a case in which the screen switching button 1024 of FIG. 12 is operated, the viewer 150 displays, on the display, a second fundus image display screen 1000B that is illustrated in FIG. 13.

Because the first fundus image display screen 1000A and the second fundus image display screen 1000B have substantially similar contents, the same portions are denoted by the same reference numerals, and description thereof is omitted, and only the different portions are described.

Instead of the original UWF fundus image display box 1032A and the post-sharpening-processing UWF fundus image display box 1032B, the second fundus image display screen 1000B has an original UWF fundus image portion displaying box 1032C and a post-sharpening-processing UWF fundus image portion displaying box 1032D.

The size of the image display box, in which the original UWF fundus image portion displaying box 1032C and the post-sharpening-processing UWF fundus image portion displaying box 1032D are combined, is the same as the sizes of the UWF fundus image display box 1032A and the UWF fundus image display box 1032B of FIG. 12.

A slide bar 1032E is provided at the border between the original UWF fundus image portion displaying box 1032C and the post-sharpening-processing UWF fundus image portion displaying box 1032D.

As indicated by arrow 1032F, the slide bar 1032E can move toward the original UWF fundus image portion displaying box 1032C side (leftward in FIG. 13) and toward the post-sharpening-processing UWF fundus image portion displaying box 1032D side (rightward in FIG. 13).

In a case in which the slide bar 1032E is moved leftward in FIG. 13, the range of the UWF fundus image portion displaying box 1032C becomes narrow, and the range of the UWF fundus image portion displaying box 1032D becomes wide. In a case in which the slide bar 1032E is moved rightward in FIG. 13, the range of the UWF fundus image portion displaying box 1032C becomes wide, and the range of the UWF fundus image portion displaying box 1032D becomes narrow.

In a case in which the screen switching button 1024 of FIG. 13 is operated, the viewer 150 displays, on the display, a second fundus image display screen 1000C that is illustrated in FIG. 14.

Because the second fundus image display screen 1000B and the third fundus image display screen 1000C have substantially similar contents, the same portions are denoted by the same reference numerals, and description thereof is omitted, and only the different portions are described.

Instead of the original UWF fundus image portion displaying box 1032C and the post-sharpening-processing UWF fundus image portion displaying box 1032D of FIG. 13, the third fundus image display screen 1000C has a display-together box 1032G.

In the display-together box 1032G, the post-sharpening-processing UWF fundus image G2 is displayed in portion 1032G2 excluding the frame. In portion 1032G1 that is separated by the frame, the portion of the original UWF fundus image that corresponds to the portion separated by the frame is displayed.

At the frame itself, for example, if portions that are other than the corners of the frame is clicked on, the display-together box 1032G can move. If a corner of the frame is dragged, the size of the frame also can be enlarged or reduced.

In this way, the post-sharpening-processing UWF fundus image G2 is disposed in the portion 1032G2 that is other than the frame, and the corresponding portion of the original UWF fundus image is displayed in the portion 1032G1 that is separated by the frame. Accordingly, the ophthalmologist can, while confirming the post-sharpening-processing UWF fundus image G2 overall, confirm, at a portion thereof, the contents before the image processing.

Note that, for example, in a case in which any portion of the display-together box 1032G is clicked-on, or in a case in which an invert button is provided and the invert button is operated, a portion of the original UWF fundus image is displayed in the portion 1032G2 other than the frame, and the post-sharpening-processing UWF fundus image G2, which corresponds to the portion separated by the frame, is displayed in the portion 1032G1 separated by the frame.

As described above, in the technique of the present disclosure, the sharpening processing section 2060 executes CLAHE processing, by using parameters corresponding to respective regions, on the respective L*a*b* components of the images of the central region and the peripheral region. Specifically, the sharpening processing section 2060 executes CLAHE processing on the respective L*a*b* components of the image of the central region at the first tile size Tc, and on the respective L*a*b* components of the image of the peripheral region at the second tile size Tp.

In the original UWF fundus image G1 (FIG. 7) that is obtained by imaging in an imaging field angle of 160° or more that is an internal illumination angle as described above, distortion of the image is greater at the peripheral region than at the central region. In other words, the surface area of the actual fundus, which corresponds to a portion of the same predetermined surface area in the original UWF fundus image G1, is greater at the peripheral region than at the central region.

Thus, in the present embodiment, the second tile size Tp is made to be a size that is greater than the first tile size Tc.

Specifically, $Tp=n^2Tc$, given that the surface area of the actual fundus that corresponds to a portion of the central region in the original UWF fundus image G1 is Sc, and that the surface area of the actual fundus that corresponds to a portion of the peripheral region in the original UWF fundus image G1 is Sp, and that $Sp=n^2Sc$.

Accordingly, the degree of enhancement by CLAHE processing with respect to the respective L*a*b* components of the image of the peripheral region, is made to be greater than the degree of enhancement by CLAHE processing with respect to the respective L*a*b* components of the image of the central region.

In this way, in the present embodiment, CLAHE processing is executed by using parameters corresponding to the central region and the peripheral region. Therefore, as compared with a case in which CLAHE processing is executed equally by using a fixed parameter for the respective regions, the thicknesses of the blood vessels that are enhanced at the respective regions can be standardized, and, due thereto, the contrast of the image at the respective regions can be standardized, and the image can be sharpened.

By the way, in the technique of the present disclosure, the sharpening processing section 2060 may execute sharpening processing on the UWF fundus image of the RGB color space. However, in the present embodiment, the sharpening processing section 2060 converts the UWF fundus image of the RGB color space into images of the L*a*b* color space, and executes sharpening processing on the respective images of the L*a*b* color space.

In sharpening processing on a UWF fundus image of the RGB color space, sharpening processing is executed only with respect to the lightness (brightness).

However, in sharpening processing on an image in the L*a*b* color space, the sharpening processing section 2060 executes sharpening processing not only on the L* value (lightness), but also on the hue and saturation for redness and greenness as a*, and for yellowness and blueness as b*. Accordingly, the luminance, hue and saturation are enhanced. Accordingly, the UWF fundus image can be made even more sharp.

A modified example of the sharpening processing of step 504 of FIG. 5 is described next with reference to FIG. 15.

In the sharpening processing of the above-described embodiment (see FIG. 6A), the sharpening processing section 2060 extracts the image of the central region and the image of the peripheral region from the fundus image, and executes CLAHE processing on the extracted image of the peripheral region and the extracted image of the central region, such that the degree of enhancement is made greater for the former than for the latter.

The technique of the present disclosure is not limited to this. For example, the sharpening processing section 2060 executes CLAHE processing in which the degrees of enhancement are different, respectively on the image G11 of the L*component (see FIG. 8A), the image of the a* component, and the image of the b* component, and generates a first image and a second image for each component, and combines the first image and the second image in a predetermined combining ratio. Specifically, the sharpening processing section 2060 combines the first image and the second image of each component such that, the further that pixel is positioned away from the center toward the periphery, the greater the proportion of the second image than the proportion of the first image. More specifically, processing is carried out as follows.

In step 602, the sharpening processing section 2060 converts the UWF fundus image G1 of the RGB color space (see FIG. 7) into images of the L*a*b* color space. Due thereto, the L* component image G11 (see FIG. 8A), the a* component image, and the b* component image are obtained.

In step 607, the sharpening processing section 2060 sets a first parameter for the image of the central region, as a parameter of the CLAHE processing. Note that the first parameter is the same as the first parameter of step 606 of FIG. 6A.

In step 609, the sharpening processing section 2060 generates a first processed image for each of the components, by executing CLAHE processing on the respective components of the entire image of the L*a*b* color space by using the first parameter.

In step 613, the sharpening processing section 2060 sets a second parameter for the image of the peripheral region, as a parameter of the CLAHE processing. Note that the second parameter is the same as the second parameter of step 612 of FIG. 6A.

In step 615, the sharpening processing section 2060 generates a second processed image for each of the components, by executing CLAHE processing on the respective components of the entire image of the L*a*b* color space by using the second parameter.

In step 617, the sharpening processing section 2060 carries out combining such that, for each pixel of the first processed image and the second processed image for each component of the image of the L*a*b* color space, the further away the pixel is positioned from the center toward the periphery, the greater the proportion of the second processed image than the proportion of the first processed image.

For example, at the center, first processed image:second processed image=1:0, and, at the outermost periphery, first processed image:second processed image=0:1. The further the position from the center toward the outermost periphery, the more that the proportion of the first processed image becomes less than 1 and the proportion of the second processed image becomes greater than 0.

In step 619, the sharpening processing section 2060 converts the respective components of the image of the L*a*b* color space, in which the first processed image and the second processed image have been combined, into an image of the RGB color space.

As described above, in the modified example illustrated in FIG. 15, for each of the components, the first image and the second image are combined in a predetermined combining ratio, and the sharpening processing section 2060 combines the first image and the second image of each component such that the further the position of the pixel from the center toward the periphery, the greater the proportion of the second image than the proportion of the first image.

The technique of the present disclosure is not limited to this, and the sharpening processing section 2060 may combine the first image and the second image of each component such that, at the central region, the proportion of the first image is greater than the proportion of the second image, and, at the peripheral region, the proportion of the second image is greater than the proportion of the first image.

In the above-described respective examples, tile size is used as the parameter of the CLAHE processing. However, the technique of the present disclosure is not limited to this, and the stretch factor can be used.

Here, the stretch factor is a limiting value that is a factor that determines the degree of enhancement of the light/dark contrast with respect to the image.

The stretch factors are made to be values corresponding to the respective regions that are the central region and the peripheral region. Specifically, the stretch factors are made to be a first stretch factor for the central region, and a second stretch factor for the peripheral region. The second stretch factor is greater than the first stretch factor. Because the effects of aberration are greater the further from the central region toward the peripheral region, the UAW fundus image G1 appears as if the sharpness thereof deteriorates the further from the central region toward the peripheral region. Thus, in order to make the contrast enhancement greater the further toward the peripheral region, the second stretch factor is made to be greater than the first stretch factor.

In the above-described respective examples, CLAHE processing is used as the sharpening processing. However, the technique of the present disclosure is not limited to this, and, for example, unsharp masking (frequency processing) may be used.

Further, a contrast enhancing processing that is different than CLAHE processing, e.g., deconvolution, histogram equalization, haze removal, shade correction, de-noising or the like, or processings that combine these may be used.

In unsharp masking, a sharpening parameter is used. The sharpening parameter is a coefficient that determines the degree of enhancement of the light/dark contrast with respect to the image.

Unsharp masking is processing that enhances the high-frequency components of the image.

By intentionally smoothing the original image (blurring the image), and creating a difference image of the original image, sharp components of the original image are created. Sharpening of the original image is carried out by adding this difference image to the original image. The constant that determines the proportion by which the difference image is added to the original image is the unsharpening parameter.

In a case in which unsharp masking is employed, in step 606 of FIG. 6A, the sharpening processing section 2060 sets a first sharpening parameter as the sharpening parameter of the unsharp masking on the image of the central region. In step 608, the sharpening processing section 2060 executes unsharp masking on the respective L*a*b* components of the image of the central region by using the first sharpening parameter. In step 612, the sharpening processing section 2060 sets a second sharpening parameter as the sharpening parameter of the unsharp masking on the image of the peripheral region. In step 608, the sharpening processing section 2060 executes unsharp masking on the respective L*a*b* components of the image of the peripheral region by using the second sharpening parameter. The second sharpening parameter is greater than the first sharpening parameter. Because the effects of aberration are greater at the peripheral region than at the central region, the second sharpening parameter is made to be greater than the first sharpening parameter in order to make the effects of aberration at the peripheral region smaller than the central region.

Moreover, the sharpening processing section 2060 may execute both CLAHE processing and unsharp masking as sharpening processings. In this case, the parameters of at least one of the CLAHE processing and the unsharp masking may be values corresponding to the respective regions that are the central region and the peripheral region.

For example, the parameters of both the CLAHE processing and the unsharp masking may be made to be values corresponding to the respective regions that are the central region and the peripheral region, or the parameters of the CLAHE processing may be made to be uniform at the central region and the peripheral region and, in the unsharp masking, the parameters may be made to be values corresponding to the respective regions that are the central region and the peripheral region. Specifically, for example, the tile sizes of the CLAHE processing are made to be constant (a tile size between the tile size Tc and the tile size Tp) at the central region and the peripheral region, and, in the unsharp masking, a first sharpening parameter is set for the central region, and a second sharpening parameter is set for the peripheral region. It is easier for the peripheral region to become blurred than the central region (the image blurs due to the effects of aberration of the optical system that images the fundus, or aberration due to the entry angle of the light beam into the pupil of the eyeball being large or the like, or the like). Therefore, is preferable to make the second sharpening parameter larger than the first sharpening parameter, and to make is such that even more of the sharp components are added.

Moreover, a contrast enhancing processing or the like other than CLAHE processing may be executed in place of at least one of, or together with the at least one of, CLAHE processing and unsharp masking. In this contrast enhancing processing other than CLAHE processing, the extent of enhancing is made to be greater at the peripheral region than at the central region, in accordance with the respective regions that are the central region and the peripheral region.

In the above-described examples, the regions having different parameters in the sharpening processing are the two regions that are the central region and the peripheral region, but the technique of the present disclosure is not limited to this, and there may be three or more plural regions. Specifically, the sharpening processing section 2060 may execute sharpening processing by using parameters that are larger the further from the center, at three or more plural regions.

In the above-described examples, the UWF fundus image G1 is transmitted to the server 140 from the ophthalmic device 110 that has a SLO system. However, the technique of the present disclosure is not limited to this. For example, a fundus camera may be connected to the network 130, and a fundus image of a smaller field angle than the ophthalmic device 110 that has a SLO system may also be transmitted from this fundus camera to the server 140. In this case, the ophthalmic device 110 transmits the UWF fundus image G1 to the server 140 in correspondence with a flag expressing that this is a UWF fundus image, and the fundus camera transmits a fundus image in correspondence with a flag expressing that this is not a UWF fundus image. On the basis of the flag expressing that this is a UWF fundus image and the flag expressing that this is not a UWF fundus image, the server 140 judges whether or not the image, which is the object of processing and corresponds to the patient ID, is a UWF fundus image. In a case in which the server 140 judges that the image that is the object of processing is a UWF fundus image, the server 140 executes the image processing of FIG. 5.

Note that the ophthalmic device 110 may transmit the UWF fundus image G1 to the server 140 in correspondence with a flag expressing that this is a UWF fundus image, and the fundus camera may transmit the fundus image without correspondence to a flag.

Conversely, the ophthalmic device 110 may transmit the UWF fundus image G1 to the server 140 without correspondence to a flag, and the fundus camera may transmit the fundus image in correspondence with a flag expressing that this is not a UWF fundus image.

In the above-described example, the image processing of FIG. 5 is executed by the server 140, but the technique of the present disclosure is not limited to this. For example, the image processing of FIG. 5 may be executed by the ophthalmic device 110 or the viewer 150, or a different image processing device may be further connected to the network 130, and this image processing device may execute the image processing.

The above-described respective examples illustrate, as examples, cases in which the image processing is realized by software structures using a computer. However, the technique of the present disclosure is not limited to this. For example, instead of software structures using a computer, the image processing may be executed by only a hardware structure such as an FPGA (Field-Programmable Gate Array) or an ASIC (Application Specific Integrated Circuit) or the like. Some of the processings of the image processing may be executed by software structures, and the remaining processings may be executed by hardware structures.

In this way, the technique of the present disclosure includes cases in which image processing is realized by software structures using a computer, and cases in which image processing is realized by structures that are not software structures using a computer. Therefore, the technique of the present disclosure includes the following first technique and second technique.

An image processing device including:
  an acquiring section that acquires a fundus image;
  an executing section that executes a first enhancing processing on an image of at least a central region of the fundus image, and executes a second enhancing processing, which is different than the first enhancing processing, on an image of at least a peripheral region of the fundus image that is at a periphery of the central region; and
  a generating section that generates an enhanced image of the fundus image on the basis of a first image obtained due to the first enhancing processing having been executed and a second image obtained due to the second enhancing processing having been executed.

Note that the sharpening processing section 2060 of the above-described embodiments is an example of the "acquiring section", "executing section" and "generating section" of the above-described first technique.

The following second technique is proposed from the disclosed contents described above.

An image processing method including:
  an acquiring section acquiring a fundus image;
  an executing section executing a first enhancing processing on an image of at least a central region of the fundus image, and executing a second enhancing processing, which is different than the first enhancing processing, on an image of at least a peripheral region of the fundus image that is at a periphery of the central region; and
  a generating section generating an enhanced image of the fundus image on the basis of a first image obtained due to the first enhancing processing having been executed and a second image obtained due to the second enhancing processing having been executed.

The following third technique is proposed from the disclosed contents described above.

A computer program product for image processing, wherein
  the computer program product has a computer-readable storage medium that itself is not a transitory signal,
  a program is stored on the computer-readable storage medium, and
  the program causes a computer to execute:
  acquiring a fundus image;
  executing a first enhancing processing on an image of at least a central region of the fundus image, and executing a second enhancing processing, which is different than the first enhancing processing, on an image of at least a peripheral region of the fundus image that is at a periphery of the central region; and
  generating an enhanced image of the fundus image on the basis of a first image obtained due to the first enhancing processing having been executed and a second image obtained due to the second enhancing processing having been executed.

The above-described image processings are merely examples. Accordingly, it goes without saying that unnecessary steps may be deleted, new steps may be added or the order of processings may be rearranged, within a scope that does not depart from the gist.

All publications, patent applications, and technical standards mentioned in the present specification are incorporated by reference into the present specification to the same extent as if such individual publication, patent application, or technical standard was specifically and individually indicated to be incorporated by reference.

The invention claimed is:

1. An image processing method, comprising:
  by a processor:
  acquiring a fundus image;
  performing a first enhancement processing on an image of at least a central region of the fundus image, and performing a second enhancement processing, which is different from the first enhancement processing, on an image of at least a peripheral region of the fundus image that is at a periphery of the central region; and
  generating an enhanced image of the fundus image by combining, at a predetermined combination ratio, a first image obtained as a result of the first enhancement processing having been performed and a second image obtained as a result of the second enhancement processing having been performed, the predetermined combination ratio being a combination ratio such that, the further a pixel is positioned from a center toward the periphery, the greater a proportion of the second image relative to a proportion of the first image.

2. The image processing method of claim 1, wherein the fundus image is a fundus image of a color space having three components that are a brightness component that expresses lightness, and a first color component and a second color component that respectively express two different shades.

3. The image processing method of any one of claim 1, wherein a degree of enhancement by a parameter of the second enhancement processing is greater than a degree of enhancement by a parameter for the first enhancement processing.

4. The image processing method of any one of claim 1, wherein the first enhancement processing and the second enhancement processing enhance contrast in an image.

5. The image processing method of claim 1, wherein:
  the fundus image is a first fundus image at which an internal illumination angle is greater than or equal to a predetermined value, or a second fundus image at which an internal illumination angle is less than the predetermined value, and the processor performs the first enhancement processing and the second enhancement processing only in a case in which the fundus image is the first fundus image.

6. The image processing method of claim 1, wherein the fundus image is an image obtained by converting a three-primary-color fundus image of an RGB color space into a complementary color space fundus image of an L*a*b* color space.

7. An image processing method, comprising:
by a processor:
acquiring a fundus image;
generating a first sharpened image by performing a first sharpening processing using a first parameter on an entire region of the fundus image, and generating a second sharpened image by performing a second sharpening processing using a second parameter, which is different from the first parameter, on the entire region of the fundus image; and
generating a sharpened fundus image by generating a sharpened central image by combining the first sharpened image and the second sharpened image at a first combination ratio, and by generating a sharpened peripheral image of a peripheral region of the sharpened central image by combining the first sharpened image and the second sharpened image at a second combination ratio that is different from the first combination ratio.

8. The image processing method of claim 7, wherein:
the first parameter and the second parameter represent sizes of regions on which the first sharpening processing and the second sharpening processing are performed, and
the first sharpening processing and the second sharpening processing are performed per region.

9. The image processing method of claim 7, wherein the first sharpening processing and the second sharpening processing comprise CLAHE processing.

10. The image processing method of claim 7, wherein the sharpened fundus image is a fundus image in a complementary color space.

11. The image processing method of claim 10, wherein the complementary color space is an L*a*b* complementary color space.

12. The image processing method of any one of claim 7, further comprising:
converting the sharpened fundus image to an RGB space; and
outputting the sharpened fundus image that has been converted to the RGB space.

13. An image processing device, comprising a processor, and a memory coupled to the processor, the processor being configured to:
acquire a fundus image;
perform a first enhancement processing on an image of at least a central region of the fundus image, and perform a second enhancement processing, which is different from the first enhancement processing, on an image of at least a peripheral region of the fundus image that is at a periphery of the central region; and
generate an enhanced image of the fundus image by combining, at a predetermined combination ratio, of a first image obtained as a result of the first enhancement processing having been executed and a second image obtained as a result of the second enhancement processing having been performed, the predetermined combination ratio being a combination ratio such that, the further a pixel is positioned from a center toward the periphery, the greater a proportion of the second image relative to a proportion of the first image.

14. An image processing device, comprising a processor, and a memory coupled to the processor, wherein the processor:
acquires a fundus image;
generates a first sharpened image by performing a first sharpening processing using a first parameter on an entire region of the fundus image, and generating a second sharpened image by performing a second sharpening processing using a second parameter, which is different from the first parameter, on the entire region of the fundus image; and
generates a sharpened fundus image by generating a sharpened central image by combining the first sharpened image and the second sharpened image at a first combination ratio, and by generating a sharpened peripheral image of a peripheral region of the sharpened central image by combining the first sharpened image and the second sharpened image at a second combination ratio that is different from the first combination ratio.

* * * * *